United States Patent [19]

Taguchi et al.

[11] Patent Number: 4,725,688

[45] Date of Patent: Feb. 16, 1988

[54] LIQUID CRYSTAL COMPOUND

[75] Inventors: Masaaki Taguchi; Takamasa Harada, both of Tokyo; Hitoshi Suenaga, Hyogo, all of Japan

[73] Assignees: Seiko Instruments Inc., Tokyo; Teikoku Chemical Industry Co., Ltd., Osaka, both of Japan

[21] Appl. No.: 830,530

[22] PCT Filed: May 30, 1985

[86] PCT No.: PCT/JP85/00302

§ 371 Date: Feb. 6, 1986

§ 102(e) Date: Feb. 6, 1986

[87] PCT Pub. No.: WO86/00087

PCT Pub. Date: Jan. 3, 1986

[30] Foreign Application Priority Data

| Jun. 7, 1984 | [JP] | Japan | 59-117209 |
| Jul. 9, 1984 | [JP] | Japan | 59-141700 |
| Jul. 11, 1984 | [JP] | Japan | 50-144027 |
| Oct. 15, 1984 | [JP] | Japan | 59-215367 |
| Nov. 27, 1984 | [JP] | Japan | 59-250171 |
| Nov. 27, 1984 | [JP] | Japan | 59-250172 |
| Mar. 4, 1985 | [JP] | Japan | 60-42116 |
| Mar. 4, 1985 | [JP] | Japan | 60-42117 |
| Mar. 20, 1985 | [JP] | Japan | 60-56652 |

[51] Int. Cl.⁴ .................. C09K 19/34; G02F 1/13; C07D 239/26

[52] U.S. Cl. .................. 544/298; 544/242; 544/335; 252/299.01; 252/299.5; 252/299.61; 350/350 R; 350/350 S

[58] Field of Search .......... 544/298, 242, 335; 252/299.61, 299.5, 299.01; 350/350 S, 350 R

[56] References Cited

U.S. PATENT DOCUMENTS

| 3,997,536 | 12/1976 | Boller et al. | 252/299.61 |
| 4,180,475 | 12/1979 | Schadt et al. | 252/299.61 |
| 4,309,539 | 1/1982 | Boller et al. | 252/299.61 |
| 4,311,610 | 1/1982 | Zaschke et al. | 252/299.61 |
| 4,389,329 | 6/1983 | Boller et al. | 252/299.61 |
| 4,402,849 | 9/1983 | Krause et al. | 252/299.61 |
| 4,410,445 | 10/1983 | Baur et al. | 252/299.5 |
| 4,462,923 | 7/1984 | Boller et al. | 252/299.61 |
| 4,564,694 | 1/1986 | Hirai et al. | 252/299.61 |
| 4,576,732 | 3/1986 | Isogai et al. | 252/299.65 |
| 4,613,209 | 9/1986 | Goodby et al. | 252/299.65 |
| 4,657,695 | 4/1987 | Saito et al. | 252/299.61 |

FOREIGN PATENT DOCUMENTS

| 84194 | 7/1983 | European Pat. Off. | 252/299.61 |
| 151446 | 8/1985 | European Pat. Off. | 252/299.61 |
| 2257588 | 6/1973 | Fed. Rep. of Germany | 252/299.61 |
| 3315295 | 10/1984 | Fed. Rep. of Germany | 252/299.61 |
| 3404117 | 8/1985 | Fed. Rep. of Germany | 252/299.61 |
| 3404116 | 8/1985 | Fed. Rep. of Germany | 252/299.61 |
| 3515373 | 11/1986 | Fed. Rep. of Germany | 252/299.61 |
| 3515374 | 11/1986 | Fed. Rep. of Germany | 252/299.61 |
| 60-255779 | 12/1985 | Japan | 252/299.61 |
| 61-85368 | 4/1986 | Japan | 252/299.61 |
| 61-189274 | 8/1986 | Japan | 252/299.61 |
| 61-215375 | 9/1986 | Japan | 252/299.61 |
| 61-271279 | 12/1986 | Japan | 252/299.61 |
| WO85/01295 | 3/1985 | PCT Int'l Appl. | 252/299.61 |
| WO86/00067 | 1/1986 | PCT Int'l Appl. | 252/299.61 |
| WO86/04328 | 7/1986 | PCT Int'l Appl. | 252/299.62 |
| WO86/06401 | 11/1986 | PCT Int'l Appl. | 252/299.61 |

OTHER PUBLICATIONS

Demus, D., et al., Flüssige Kristalle in Tabellen II, Veb Deutscher Verlag für Grundstoffindustrie, Leipzig, pp. 342-400, (1984).

Zaschke, H., Advances in Liquid Crystal Research & Applications, Bata, L., Ed., Pergamon Press, Oxford, pp. 1059-1074, (1980).

Gray, G. W., et al., Liquid Crystals & Plastic Crystals, vol. 1, John Wiley & Sons, New York, pp. 137-143, (1974).

*Primary Examiner*—Teddy S. Gron
*Attorney, Agent, or Firm*—Bruce L. Adams; Van C. Wilks

[57] ABSTRACT

The present invention is an optically active liquid crys- (Abstract continued on next page.)

tal compound shown in the following general formula;

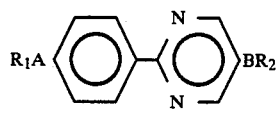

[wherein, A and B respectively show one of —, —O—, 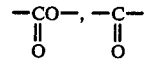

(— shows direct bond), one of $R_1$ and $R_2$ shows direct chain alkyl group and the other one shows either alkyl group having asymmetric carbon atom or alkoxy alkyl group having asymmetric carbon atom and ether bonding. Also, onto the asymmetric carbon atom, one of the groups —$CH_3$, —CN, —Cl is added.]

It is clear that there are many compounds in these liquid crystal compounds, that show Sm C* phase in a wide temperature range close to room temperature and that have high response speed.

78 Claims, 8 Drawing Figures

LIQUID CRYSTAL COMPOUND

FIELD OF THE INVENTION

The present invention is related to a new liquid crystal compound useful for electric optical elements, utilizing the response of a ferroelectric smectic liquid crystal to an electric field.

BACKGROUND OF THE INVENTION

Liquid crystals have been adapted already as the electric optical elements for many kinds of devices such as display devices, shutter alley for a printer, shutters for cameras, and are actuated in the display of watches and table calculators.

Most of the liquid crystal display elements presently actualized are elements utilizing the dielectric orientation efficiency of a nematic liquid crystal or a cholesteric liquid crystal. But, concerning the expected requirements for display elements with many picture elements, there are such problems as, an insufficient response ability, a contrast not able to obtain the necessary drive margin, and an insufficient visual angle characteristic. Therefore, extensive research and development of the TFT panel or MOS panel that forms the switching element in each picture element is being carried out.

In this state, Clark et al (U.S. Pat. No. 4,367,924) conceived new a liquid crystal element with new display principle, utilizing the smectic phase, which cures the above defects of the liquid crystal element. The explanation of this new element is as follows;

FIG. 1 is a typical diagram of the smectic C* phase or the smectic H phase. The liquid crystal is composed of molecule layers 1, and in each of the layers, the average direction of the molecule axis is inclined o degrees in the vertical direction to the layers. Meyer et al teaches in a thesis titled "Ferroelectric liquid crystal" of "Physical Journal" (Le Journal de Physique Vol. 36, March, 1975 PPL-69 to L-71), that, the Smectic C* or H phase composed of an optically active molecule generally has an electric dipole density P and is ferroelectric. This dipole density P is vertical to the molecule direction n, and is parallel to the layer surface of the smectic. What they teach is adaptable to the smectic H phase, but in the H phase, the viscosity to the rotation around the axis vertical to the layer, becomes large. The existence of electric dipoles in these chiral smectic liquid crystals gives a stronger coupling force to the electric field, than that of dielectric anisotropy. Furthermore, it can be said that this coupling force has a polarity characteristic, in the sense that the favorable direction of P is the parallel direction to electric field E, and so, by reversing the direction of the applied electric field, the direction of P can also be reversed.

Therefore, by reversing the electric field, as shown in FIG. 2, the direction of the molecule can be controlled by moving the molecule along the cone (the angle 2° of this cone is hereinafter referred to as the cone angle). Then, by detecting the variation of the average molecule axis direction with two polarizers, the liquid crystal element can be utilized an electric optical element.

Because this electric optical element which utilizes the response of the Smectic C or H phase to an electric field, holds a coupling force between its spontaneous polarization and the electric field, a force which is 3 or 4 orders larger than the coupling force of dielectric anisotropy, compared to TN type liquid crystal element, this electric optical element has an efficient high speed response characteristic, and it can also have a memorizing characteristic by selecting the appropriate orientation control; thus it is expected to be adapted as a high speed optical shutter or as a display with a large capacity for information.

Meanwhile, many kinds of chiral smectic liquid crystal material having a ferroelectric characteristic have been studied and synthesized. The first synthesized ferroelectric liquid crystal is called DOBAMBC.

p-Decyloxybenzilidene-p'-amino-2- methylbutyl cinnamate, and many compounds of this series of liquid crystal compositions, shown in the following formula, have been synthesized for research concerning ferroelectric liquid crystals.

wherein X represents H, Cl, or CN and Y represents Cl.

But as this series of liquid crystal shows the chiral smectic phase at a temperature higher than room temperature, there are such defects as, not being able to be used at room temperature, it is a Schiff base series, it is decomposed with water, and its stability is bad.

As a developed compound of this series, a Schiff base series chiral smectic liquid crystal compound in which the hydroxyl group is introduced into one of the benzene rings, and provides a hydrogen bond in the molecule, as shown in the following general formula, was announced by B. I. Ostrovskii ("ferroelectric", 24,1980,309) and by A. Hallsby (Molecular crystals and liquid crystals, Letter 82,1982,61), and this developed compound has been given attention as being a compound showing the smectic C* phase at a wide range of temperature including room temperature.

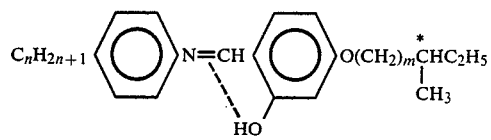

As this compound also has a hydrogen bond within the molecule, it is hardly decomposed with water and has much better stability a compared to general Shiff series of liquid crystal. But as a practical matter, it is required that the compound not crystallize at a temperature below 0° C., and so the liquid crystal material synthesized with compounds of this series are still not completely satisfactory.

Other than this, a liquid crystal material of the azoxy series was announced by P. Keller et al ([Annales de physique]1978, 139) but with this compound too, there are such practical problems as not having efficient characteristics concerning the temperature range, and being a deep yellow color.

Among these compounds, an ester series liquid crystal having a good stability and widely practiced as a TN type liquid crystal material has been given much attention. In a well known document, a liquid crystal compound has been disclosed having a structure of the formula;

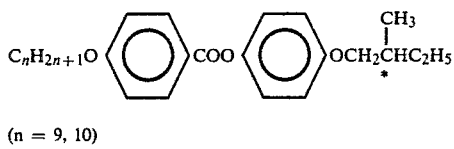

(n = 9, 10)

This formula was announced by B. I. Ostrovskii et al, as being material showing the chiral smectic liquid crystal at a temperature range close to room temperature. Also, G. W. Gray et al announced in "Molecular Crystal and Liquid Crystal" 37 (1976) 189, (1978) 37, a biphenyl ester series of compounds showing chiral smectic liquid crystal at a high temperature range.

As stated above, at present, a liquid crystal that shows a chiral smectic phase over a wide range of temperature including the practical condition of room temperature, does not exist, and, even with materials showing a chiral smectic phase at a relatively wide range of temperature, there still have been some problems in its stability.

Therefore, the present invention has an object of offering a new liquid crystal which has good stability, and is highly likely to provide a chiral smectic liquid crystal compound at a wide range of room temperature including room temperature.

DISCLOSURE OF THE INVENTION

Therefore, the present invention is a liquid crystal compound shown in the following formula;

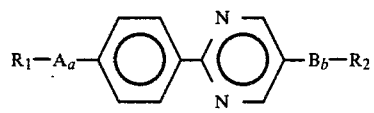

wherein A and B respectively represents one of —O—,

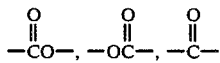

; a and b are each 0 or 1; one of $R_1$ and $R_2$ represents a normal chain alkyl group and the other represents an alkyl group having an asymmetric carbon atom or for an alkoxyalkyl group having an asymmetric carbon atom one of the groups —$CH_3$, —CN, —Cl is attached to the asymmetric carbon atom.

It is clear that many of the liquid crystal compounds shown in the above formula show the Sm C* phase at a wide temperature range including room temperature, and the response speed is very fast. It is understood that the response speed of this series of liquid crystal compounds is faster than the compound shown in the general formula;

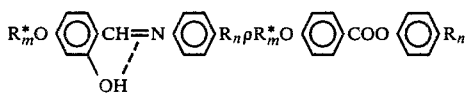

It is thought that, though the framework portion of the molecule is as short as the benzene ring and the pyrimidine ring which is directly bonded thereto the fact that the pyrimidine series liquid crystal compounds of the present invention shows a high smectic characteristic, and that they show the Sm C* phase at a wide temperature range, is because the polarization of the molecule axis direction, caused by the difference between the electric negativity of the pyrimidine ring and benzene ring, and mutual function between the molecules, are large. Also, the reason for having a high-response ability is considered to be the following: as the width of pyrimidine ring is wider than the width of benzene ring, the molecule form is inflated in the center portion, and this inflated part acts to separate the distance between the molecules, the rotation viscosity of the molecule becomes small, and thus the speed of the response becomes faster.

BEST MODE OF CARRYING OUT THE INVENTION

Figure 1:
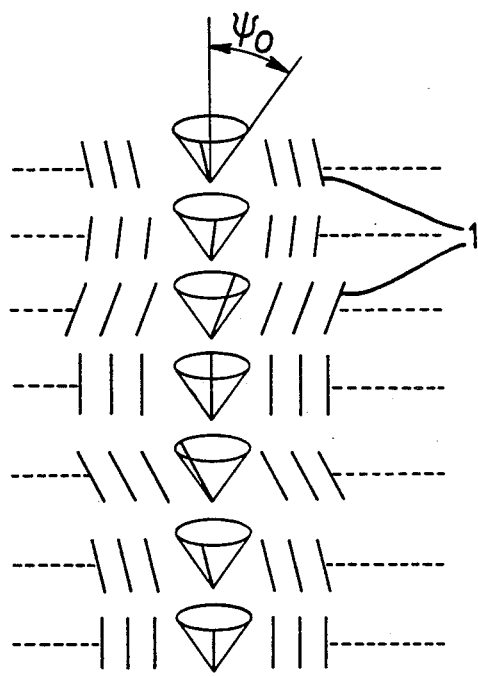
FIG. 1 is a typical diagram of the smectic C* or H phase.
Figure 2:
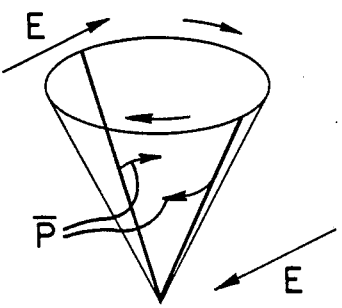
FIG. 2 is a typical drawing showing the movement of a chiral smectic phase liquid crystal molecule moving along the cone by an electric field.

The liquid crystal compound of the present invention is synthesized as follows;

Synthetic method 1

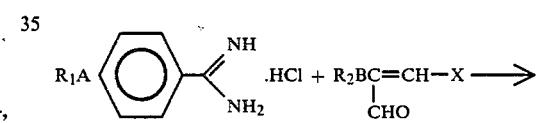

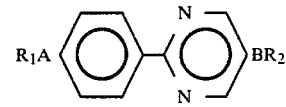

wherein: X represents a lower alkyldiamine group, hydroxyl group or lower alkoxy group.

This reaction is carried out by selecting an appropriate solvent, and by utilizing an alkali metal alcoholate, such as alkali metal sodium alcoholate, potassium t-butoxide, and and an anhydrous alkali metal salt, such as anhydrous sodium carbonate or anhydrous potassium carbonate. As the solvent utilized in this reaction, the following solvents are appropriate; alcohol such as methanol, ethanol, propanol, isopropanol, butanol, or glycols; benzene, toluene, dimethyl formamide, dimethyl sulfoxide, tetrahydrofuran, ethylene glycol dimethyl ether and diethylene glycol monomethyl ether. The reaction is carried out at room temperature, or at the reflux temperature of the solvent.

Synthetic method 2

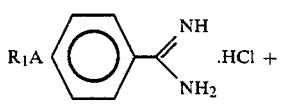

-continued
Synthetic method 2

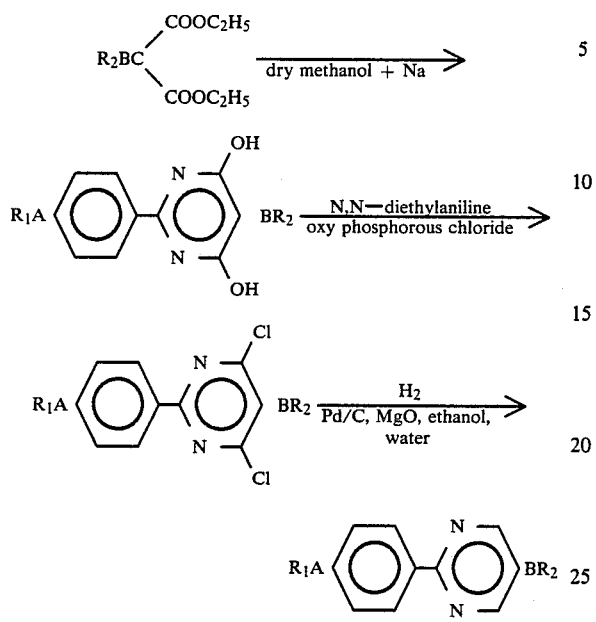

The first reaction is carried out by combining an alkali metal alcoholate and anhydrous alkali metal salt; in the second reaction, thionyl chloride, phosphorous trichloride, phosphorous pentachloride and phosphorous trichloride can be utilized other than oxy-phosphorous chloride, and N,N-diethylaniline can be replaced with a tertiary amine such as pyridine or triethylamine. Also the third reaction is a dehalogenation by the contact reduction reaction.

Here,

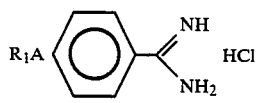

is synthesized as follows;

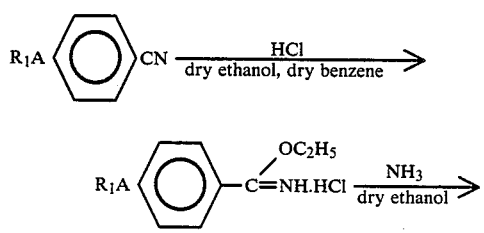

-continued

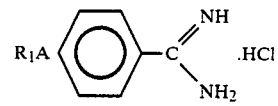

Synthetic method 3

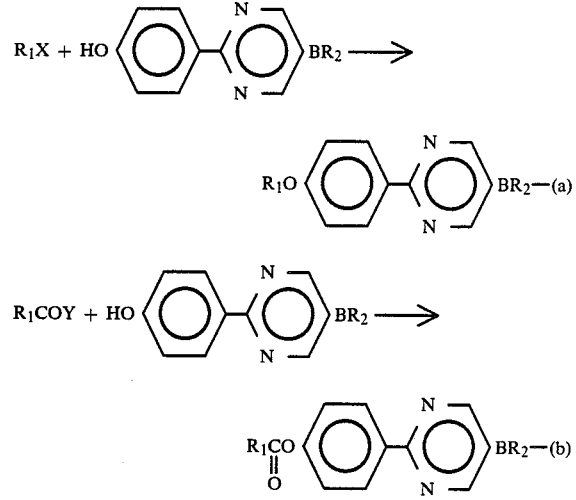

X in the above formula (a) stands for the tolylsulfonyloxy group, methyloxy group or a halogen atom; Y in the above formula (b) stands for an halogen atom or an active ester.

The reaction of formula (a) is conducted with an appropriate solvent such as N,N-dimethylformamide, dimethyl sulfoxide, toluene, xylene, dioxane, and the condensation reaction is carried out by utilizing alkali metal or alkali metal hydride.

Also, in the above reaction (b), solvents of ether series such as ethyl the ether, tetrahydrofuran; aromatic series such as benzene, toluene; the ester series such as ethyl acetate and butyl acetate; and the haloalkane series such as chloroform can be utilized, and a tertiary amine such as pyridine, triethylamine, dimethylaniline, dimethylamino pyridine can be used as catalyst, to conduct the reaction smoothly.

Here,

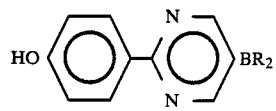

can be synthesized as follows;

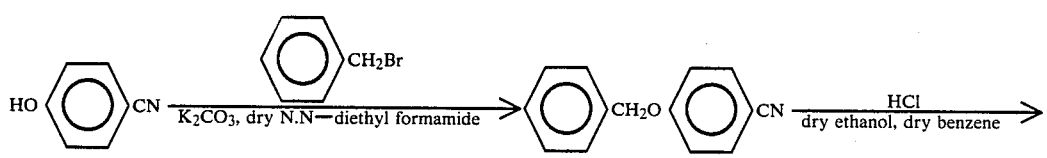

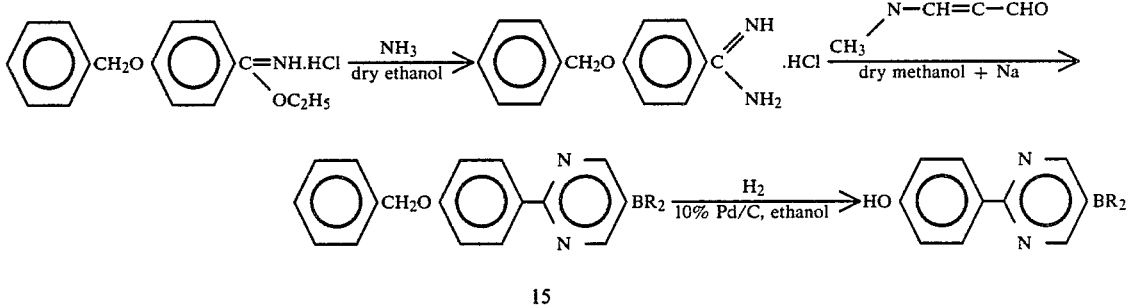

Methods to synthesize phenyl pyrimidine holding various side chains are shown above, but now we will show methods to synthesize optically active side chains.

Optically active alcohol is synthesized as follows; Utilizing active amyl alcohol $$(CH_3CH_2\overset{*}{C}HCH_2OH, [\alpha]_D^{25} = -4,487$$

(neat)) as starting material, a reaction is carried out to increase the number of carbon atoms by the alkyl malonic acid synthetic method so as to obtain, $$CH_3CH_2\overset{*}{C}H(CH_2)_m\text{—}OH$$
$$\phantom{CH_3CH_2}|\phantom{CH(CH_2)_m}\phantom{-OH}$$
$$\phantom{CH_3CH_2C}CH_3$$

The optically active alcohol thus made, can be changed to an aliphatic or aromatic compound, sulfonic acid ester, or halogenide, with the usual methods.

With this method, the asymmetric carbon atom becomes the third carbon atom counting from the edge of side chain, and, the general synthetic method for preparing optically active side chains in which an asymmetric carbon atom is positioned in another place, is as follows;

$$CH_3(CH_2)_m CH_2\overset{*}{C}H(CH_2)_n\text{—}OH \qquad (1)$$
$$\phantom{CH_3(CH_2)_mCH_2}|$$
$$\phantom{CH_3(CH_2)_mCH}CH_3$$

in the above formula, m+n is an integral number from 1 to 16, m=0 to 13, n=1 to 14, and * stands for asymmetric carbon atom To obtain the chemical compound shown in formula (1), Grignard reagent $$CH_3 (CH_2)_m \, MgX \qquad (2)$$

, where X represents a halogen atom, is made with an available alkyl halogenide and magnesium metal. While either a halide or an available optically active β-hydroxyisobutyric acid ester, by means of a method usually utilizing 47% hydrobromic acid-sulfuric acid, or by carrying out a sulfonyl ester reaction on the acetate with a reaction between alkyl (or allyl) sulfonyl halide, is changed into a compound as shown in formula (3).

$$Y\text{—}CH_2\overset{*}{C}HCOOR \qquad (3)$$
$$\phantom{Y-CH_2C}|$$
$$\phantom{Y-CH_2}CH_3$$

in the formula, Y stands for a halogen atom, p-toluen sulfonyloxy group, methanesulfonyloxy group, and * represents an asymmetric carbon atom.

Next, a coupling reaction onto the compound shown in formula (2) is carried out and the compound shown in formula (3) in the presence of a catalyst such as a metal halide, for example, primary copper iodide, primary copper bromide, or secondary iron chloride, to obtain the compound shown in formula (4).

$$CH_3(CH_2)_mCH_2\overset{*}{C}HCOOR \qquad (4)$$
$$\phantom{CH_3(CH_2)_mCH_2C}|$$
$$\phantom{CH_3(CH_2)_mCH_2}CH_3$$

In the formula, m stands for an integral number 0 to 13, R stands for a lower alkyl group such as methyl, ethyl, propyl, and * stands for an asymmetric carbon atom The compound obtained in the reaction shown in formula (4) is changed into the alcohol shown in formula (1), by reducing with lithium aluminum hydride.

In the obtained compound (1), wherein m stands for an integral number 0 to 13, n stands for 1, and * stands for an assymmetric carbon atom, the hydroxy group is changed into a halogen, methanesulfonyloxy group, or p-toluenesulfonyloxy group, by the usual halogenide reaction or by a sulfonyl esterification reaction.

The compounds obtained with the above methods lead to compounds with differently positioned asymmetric carbon atoms, by appropriately selecting and conducting the usual reaction for increasing the number of carbon atoms for example, reduction after a malonic ester synthsis, the reduction and hydrolysis, after adding a cyano group and reduction to form a carboxylic acid after a Grignard reaction.

Thereby, the optically active alkanol compound shown in formula (1) having one asymmetric carbon atom at an arbitrary position within the alkyl chain is obtained.

The obtained compound shown in formula (1) is utilized as a side chain material compound, either as it is, or by halogenizing or sulfonyl esterizing the hydroxyl group.

Because the liquid crystal compounds offered in the present invention hold one asymmetric carbon, there exists one pair of optical antipodes. These antipodes are included in the object compounds of the present invention, the optical characteristics of which are determined in the compounds shown in formula (1), by selecting which antipode to use.

An explanation of the present invention referring to the examples is as follows.

EXAMPLE 1

Synthesis of optically active (s)-5-n-octyl-2-[4-(6-methyloctyloxy)phenyl]pyrimidine (1) Synthesis of optically active (s)-4-(6-methyl octyloxy)benzonitrile.

Add 5.75 g of 4-cyanophenol 10 g of 1 brom-6-methyl octane synthesized of available active amyl alcohol, 6.67 g of anhydrous potassium carbonate, 30 ml of N,N-dimethyl formamide into 100 ml four-mouth flask under nitrogen atmosphere, allow to react for 8 hours at 110° C. After the reaction, filter the insoluble matter, then extract ether. The organic layer is then washed with 5% NaOH, water and saturated salt water, then dried and evaporated to remove the ether. Then when the obtained oily matter is refined, 11.4 g of optical (s)-4-(6-methyloctyloxy)benzonitrile is obtained.

| $\nu_{max}^{Film}$(cm$^{-1}$) | | $\delta_{TMS}^{CDCl_3}$(ppm) | |
|---|---|---|---|
| 2230 | | 6.92, dJ = 9Hz, 2H, AromaticH | |
| 1605 | | 7.57, dJ = 9Hz, 2H, AromaticH | |
| 1570 | | 3.97, tJ = 6Hz 2H, —CH$_2$—O— | |
| 1115 | | | |

(2) Synthesis of optically active (s)-4-(6-methyloctyloxy)benzamidine hydrochloric acid salt.

Add 10 g of optically active (s)-4-(6-methyloctyloxy)-benzonitrile, 12.5 ml dry ethanol, and 16 ml dry benzene into a 100 ml four-mouth flask. Agitating this mixture, bubble in dried hydrogen chloride gas at temperature below 3° C., then blow in at below 3° C. After it is left at room temperature for 2 days, evaporate and remove the solvent to obtain impure crystals.

Put the obtained rough crystal into a 300 ml four-mouth flask with 64 ml of dry ethanol, then slowly drip into the flask 30 ml of dry ethanol which includes 11.08 g ammonia, at room temperature. After dripping, it is left at room temperature for three days. This is then refined, and 9.58 g of optical (s)-4-(6-methyloctyloxy)-benzamidine hydrochloric acid salt is obtained.

| $\nu_{max}^{nujol}$ (cm$^{-1}$) | 3060 |
|---|---|
| | 1680 |
| | 1655 |
| | 1105 |

$\delta_{TMS}^{DMSO-d_6}$ (ppm) 9.4, broads, 3H, 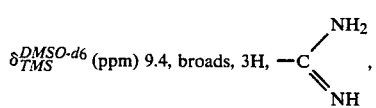

(D$_2$O exchange characteristic)
7.14, d J = 9Hz, 2H, Aromatic H
8.06, d J = 9Hz, 2H, Aromatic H
4.09, t J = 6Hz, 2H, —O—CH$_2$—

(3) Synthesis of optically active (s)-5-n-octyl-2-[4-(6-methyloctyloxy)phenyl]-4,6-dihydroxy pyrimidine.

Pour 1.15 g sodium metal, and 33 ml dry methanol into 100 ml four-mouth flask; add 5 g of optically active (s)-4-(6-methyloctyloxy)benzamidine hydrochloric acid salt, then pour 4.55 g of diethyl n-octylmalonate into this sodium methylate solution and then allow to react for 18 hours under heat and reflux conditions. After cooling, acidify the mixture utilizing concentrated sulfuric acid, and extract the crystals. The impure crystals are purified, and then optically active 6.32 g of (s)-5-n-octyl-2-[4-(6methyloctyloxy)phenyl]-4,6-dihydroxy-pyrimidine is obtained.

| $\nu_{max}^{nujol}$ (cm$^{-1}$) | 2660 |
|---|---|
| | 1664 |
| | 1610 |
| | 1110 |

(4) Synthesis of optically active (s)-5-n-octyl-2-[4-(6-methyloctyloxy)phenyl]-4,6-dichloro-pyrimidine.

Pour 6 g of optically active (s)-5-n-octyl-2-[4-(6-methyloctyloxy)phenyl]-4,6-dihydroxy-pyrimidine, 27 ml of oxyphosphorous chloride, and 4 ml of N,N-diethylaniline into a 50 ml flask, then allow to react for 21 hours under heat and reflux conditions. After the reaction, evaporate and remove the over obtained oxyphosphorus chloride, then pour into ice water. Then extract this with ether, wash with alkali water solution, then wash again with water and saturated salt water until it is neutral. After drying the organic layer, evaporate and remove the ether; then impure product is obtained. When this product is refined, 3.6 g of optically active (s)-5-n-octyl-2-[4-(6-methyloctyloxy)phenyl]-4,6-dichloro-pyrimidine is obtained.

| $\nu_{max}^{nujol}$ (cm$^{-1}$) | 1610 |
|---|---|
| | 1122 |
| | 1090 |
| $\delta_{TMS}^{CDCl_3}$ (ppm) | 8.22, d J = 9Hz, 2H, Aromatic H |
| | 6.85, d J = 9Hz, 2H, Aromatic H |
| | 3.94, t J = 6Hz, 2H, —CH$_2$—O— |

2.82, t, 2H, 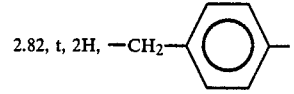

(5) Synthesis of optically active (s)-5-n-octyl-2-[4-(6-methyloctyloxy)phenyl]-pyrimidine.

Pour 1.88 g of optically active (s)-5-n-octyl-2-[4-(6-methyloctyloxy)phenyl]-4,6-dichloro-pyrimidine, 0.4 g of 10% palladium-carbon, 0.55 g of magnesium oxide, 60 ml of ethanol, and 45 ml of water, into a 200 ml flask, then add hydrogen under oil bath conditions at 50° C., until the logical amount of hydrogen has been absorbed. The catalyst is filtered and separated, then ether is extracted. After the ether layer is washed with water and with saturated salt water, and dried, the ether is evaporated. The resultant impure product is repeatedly refined, and 0.9 g of optically active (s)-5-n-octyl-2-[4-(6-methyloctyloxy)phenyl]-pyrimidine is obtained.

| $\nu_{max}^{nujol}$ (cm$^{-1}$) | 1610 |
|---|---|
| | 1584 |
| | 1110 |
| $\delta_{TMS}^{CDCl_3}$ (ppm) | 8.55, S, 2H 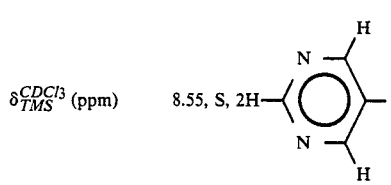 |

8.35, d J = 9Hz, 2H, Aromatic

-continued 6.94, d J = 9Hz, 2H, Aromatic
3.99, t J = 6Hz, 2H, —CH₂—O—

2.57, t, 2H, —CH₂—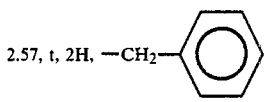

This liquid crystal compound showed a transmitting temperature as follows:

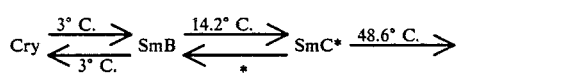

SmA $\xrightarrow{56.3° C.}$ Iso (* stands for supercooling)

To show a Sm C* phase at a wide temperature range including room temperature for a range of about 35 degrees (°C.), and also to hold a Sm B phase under the Sm C* phase, the smectic domain condition is kept until 3° C. at the low temperature side. The Sm B phase does not respond to display, but because there is no distruction of the smectic domain condition by crystallization, when at high temperature, and is turned back to the Sm C* phase, the same display condition is turned ON/OFF, so that the Sm B phase may be utilized for preservation under low temperature of LC panel time.

Figure 3:
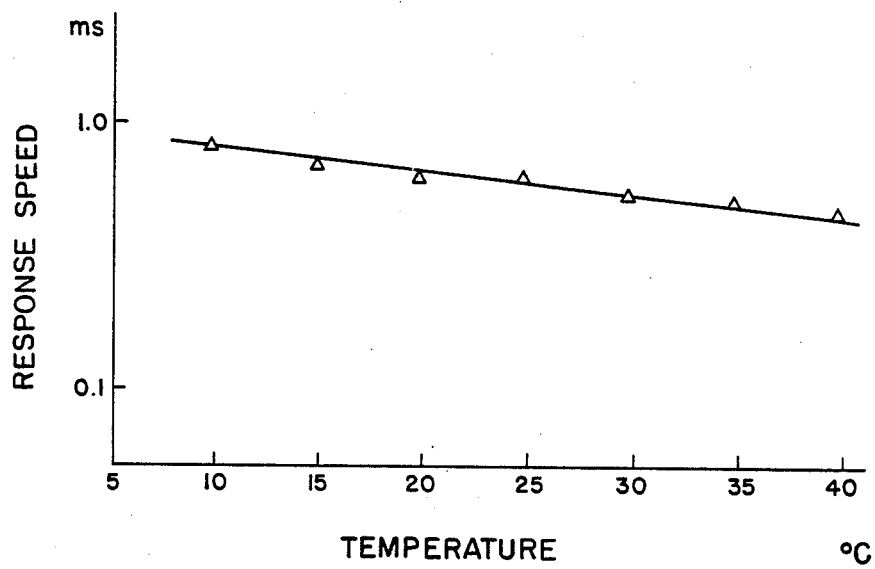
FIG. 3 is a graph showing the temperature dependance of the response speed.
Figure 8:
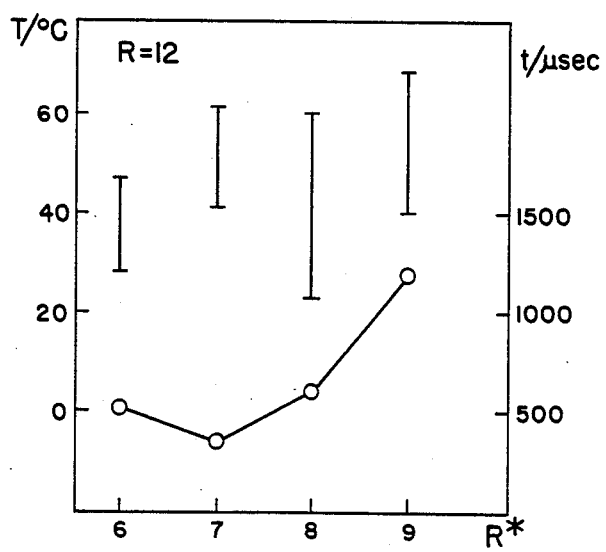
FIGS. 4 to 8 are the graphs showing the variation of response speed when n of 8 to 12 is fixed and m is variously changed.
Figure 4:
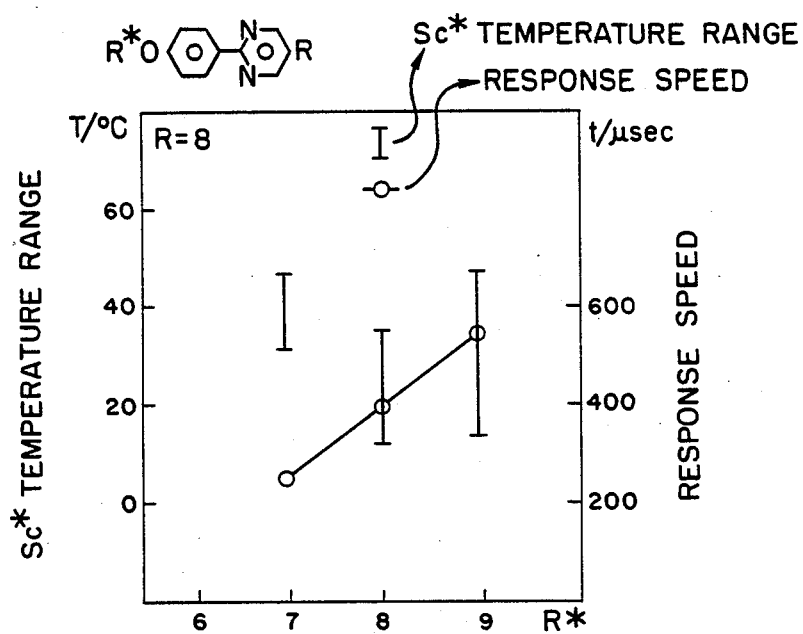
Figure 5:
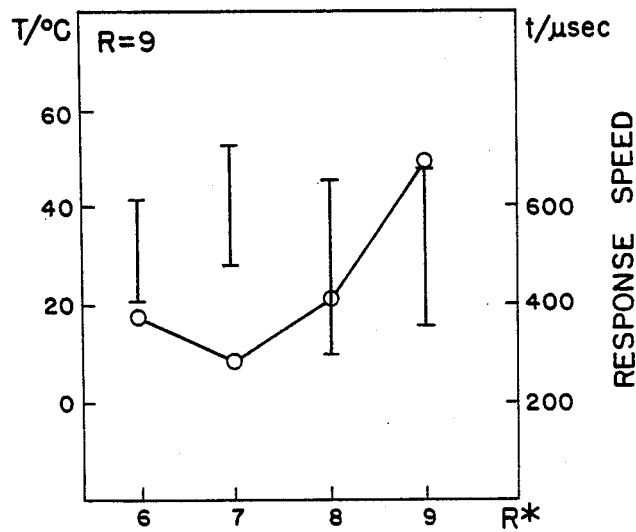
Figure 6:
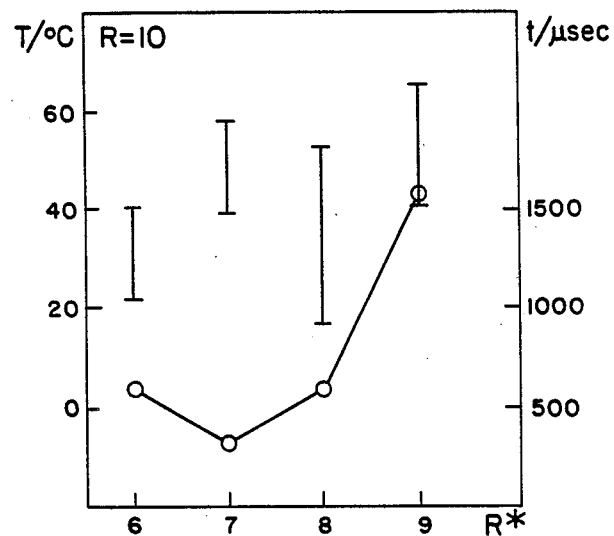
Figure 7:
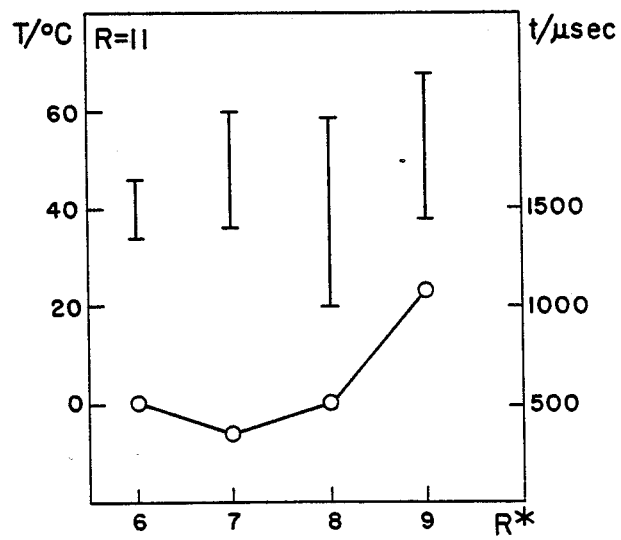

This liquid crystal compound is sandwiched between PVA rubbing one-axis orientation processed plates, and the liquid crystal layer fixed at a thickness of 2.5 μm, with ±20 V voltage applied, under orthogonal nicol, the characteristics are then determined, with the following results;
the measuring temperature is 25° C.
the cone angle 40.5° C.
contrast (T on/T off) 12.5
response speed 600μ sec.
The temperature depending data of the response of this cell is shown in FIG. 3.

EXAMPLES 2 TO 31

General Formula

In the following formula:

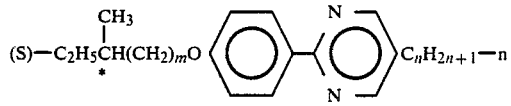

compounds with varying values of m and n are synthesized by the same method as Example 1.

The data of the transmitting temperature and the response speed measured with the same method as in example 1, is shown in Table 1.

FIGS. 4 to 8 are drawings showing the Sm C* temperature range and response speed of above compounds of Table 1, drawn in relation to the number of carbon atoms in the side chain.

TABLE 1

| example No. | m | n | phase transition temperature | response speed μsec |
|---|---|---|---|---|
| 2 | 1 | 11 | Cry $\underset{}{\overset{39.9}{\rightleftarrows}}$ Sm C $\xrightarrow{*41.4}$ Sm A $\xrightarrow{47.5}$ Iso | 260 (28.3° C.) |
| 3 | 2 | 6 | Cry $\underset{*8}{\rightleftarrows}$ $\overset{13}{\rightleftarrows}$ Ch $\overset{32}{\rightleftarrows}$ Iso | — |
| 4 | 2 | 7 | Cry $\underset{*10}{\overset{39.2}{\rightleftarrows}}$ Iso, Sm A $\nearrow^{39.2}$ | — |
| 5 | 2 | 8 | Cry $\underset{*28}{\overset{36.4}{\rightleftarrows}}$ Iso, Sm A $\nearrow^{36.4}$ | — |
| 6 | 2 | 9 | Cry $\overset{23.0}{\rightleftarrows}$ Sm X $\overset{31.0}{\rightleftarrows}$ Sm C $\xrightarrow{*38.7}$ Sm A $\xrightarrow{46.5}$ Iso | 380 (30° C.) |
| 7 | 2 | 10 | Cry $\underset{*5.8}{\overset{22}{\rightleftarrows}}$ Sm C $\xrightarrow{*41.4}$ Sm A $\xrightarrow{41.5}$ Iso | 610 (33° C.) |
| 8 | 2 | 11 | Cry $\underset{<18.2}{\overset{24.7}{\rightleftarrows}}$ Sm X $\overset{33.9}{\rightleftarrows}$ Sm C $\xrightarrow{*45.5}$ Sm A $\xrightarrow{50.0}$ Iso | 530 (39° C.) |
| 9 | 2 | 12 | Cry $\underset{*18.7}{\overset{28.5}{\rightleftarrows}}$ Sm C $\xrightarrow{*47.0}$ Sm A $\xrightarrow{51.2}$ Iso | 540 (34° C.) |
| 10 | 3 | 6 | Cry $\underset{*8.6}{\overset{25.0}{\rightleftarrows}}$ Sm X $\nearrow^{11.6}$ Ch $\overset{42.5}{\rightleftarrows}$ Iso | — |

TABLE 1-continued

| example No. | m | n | phase transition temperature | response speed μsec |
|---|---|---|---|---|
| 11 | 3 | 7 | Cry $\underset{*13.0}{\overset{28.5}{\rightleftarrows}}$ Sm C $\xrightarrow{*53.6}$ Sm A $\xrightarrow{60.0}$ Iso | 290 |
| 12 | 3 | 8 | Cry $\xrightarrow{31.2}$ Sm C $\xrightarrow{*46.8}$ Sm A $\xrightarrow{50.8}$ Iso; Cry $\overset{26.2}{\nwarrow}$ Sm B $\overset{*16.8°C.}{\nearrow}$ | 250 |
| 13 | 3 | 9 | Cry $\underset{*3.0}{\overset{23.0}{\rightleftarrows}}$ Sm X $\underset{7.0}{\overset{28.0}{\rightleftarrows}}$ Sm C $\xrightarrow{*30.0}$ Sm A $\xrightarrow{51.5}$ Ch $\xrightarrow{52.0}$ Iso | 530 |
| 14 | 3 | 10 | Cry $\underset{*12.0}{\overset{33.0}{\rightleftarrows}}$ Sm X $\xrightarrow{38.5}$ Sm C $\xrightarrow{*58.0}$ Iso | 330 |
| 15 | 3 | 11 | Cry $\underset{*}{\overset{35.9}{\rightleftarrows}}$ Sm C $\xrightarrow{*60.0}$ Iso | 380 (27.4° C.) |
| 16 | 3 | 12 | Cry $\xrightarrow{41.0}$ Sm C $\xrightarrow{*62.2}$ Iso; with Sm X (*16.5, *23.8) | 360 |
| 17 | 3 | 14 | Cry $\underset{*}{\overset{32.0}{\rightleftarrows}}$ Sm B $\underset{*29.0}{\overset{45.0}{\rightleftarrows}}$ Sm C $\xrightarrow{*59.8}$ Iso | 450 (37.2° C.) |
| 18 | 4 | 6 | Cry $\underset{*2}{\overset{-5°C.}{\rightleftarrows}}$ Sm A $\xrightarrow{27}$ Ch $\xrightarrow{42}$ Iso | — |
| 19 | 4 | 7 | Cry $\underset{*-11}{\overset{-6}{\rightleftarrows}}$ Sm A $\xrightarrow{46.3}$ Ch $\xrightarrow{49}$ Iso | — |
| 20 | 4 | 8 | Cry $\underset{*6.3}{\overset{12.0}{\rightleftarrows}}$ Sm C $\xrightarrow{*34.7}$ Sm A $\xrightarrow{49.5}$ Iso | 260 (30° C.) |
| 21 | 4 | 9 | Cry $\underset{*5}{\overset{10}{\rightleftarrows}}$ Sm C $\xrightarrow{*46.0}$ Sm A $\xrightarrow{59.0}$ Iso | 430 (35° C.) |
| 22 | 4 | 10 | Cry $\underset{*11}{\overset{17}{\rightleftarrows}}$ Sm C $\xrightarrow{*53.8}$ Sm A $\xrightarrow{63.0}$ Iso | 600 (30° C.) |
| 23 | 4 | 11 | Cry $\underset{*8}{\overset{20}{\rightleftarrows}}$ Sm C $\xrightarrow{*59.0}$ Iso | 530 (30° C.) |
| 24 | 4 | 12 | Cry $\xrightarrow{23}$ Sm C $\xrightarrow{*61.5}$ Iso; with Sm X (11.0, 16.0) | 620 (27° C.) |
| 25 | 5 | 6 | Cry $\underset{*8.0}{\overset{12.0}{\rightleftarrows}}$ Sm C $\xrightarrow{*23.8}$ Ch $\xrightarrow{45.6}$ Iso | 810 (17° C.) |
| 26 | 5 | 7 | Cry $\overset{10}{\rightleftarrows}$ Sm X $\underset{*-2}{\overset{16}{\rightleftarrows}}$ Sm C $\xrightarrow{*39.0}$ Sm A $\xrightarrow{54.0}$ Ch $\xrightarrow{61.0}$ Iso | 250 (31° C.) |
| 27 | 5 | 9 | Cry $\underset{*10.0}{\overset{16.0}{\rightleftarrows}}$ Sm C $\xrightarrow{*49.1}$ Sm A $\xrightarrow{61.0}$ Iso | 700 (31° C.) |
| 28 | 5 | 10 | Cry $\xrightarrow{41.0}$ Sm C $\xrightarrow{*61.0}$ Iso; with Sm X (30.0) | 1600 (42° C.) |

TABLE 1-continued

| example No. | m | n | phase transition temperature | response speed μsec |
|---|---|---|---|---|
| 29 | 5 | 11 | Cry ⟶ Sm B ⇌(36.7/*23.0) Sm C ⟶(*68.0) Iso | 1100 (31.5° C.) |
| 30 | 5 | 12 | Cry ⇌(40.5/29.3) Sm C ⟶(*70.0) Iso | 1200 (45° C.) |
| 31 | 5 | 14 | Cry ⇌(43.0/*) Sm B ⇌(45.0/*35.5) Sm C ⟶(*66.0) Iso | 1700 (66° C.) |

EXAMPLE 32

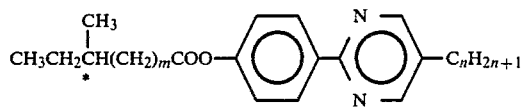

m=4, n=8, *=asymmetric carbon.

The method of synthesis of optically active (s)-5-octyl-2-[4-(6-methyloctanoneoxy)phenyl]pyrimidine is as follows.

Pour 1.78 g (62 mmol) 4-(5-octyl-2-pyrimidine)-phenol and 15 ml of dry pyrimidine into a 50 ml flask. Next, slowly drip 1.10 g (6.2 mmol) of optically active (s)-6-methyloctonic acid chloride into the flask with cooling under ice. After dripping, allow the reaction to continue for one whole day, returning the temperature to room temperature. After the reaction, pour it into ice water, then extract the product with ethyl acetate. The organic layer is successively washed with water, NH$_4$Cl, 5% NaOH, then washed again with water and saturated salt water until it becomes neutral, then dried and the solvent is filtered and removed. The obtained impure product is repeatedly refined, and 5-n-octyl-2-[4-(6-methyloctanoneoxy)phenyl]pyrimidine 1.5 g (57%) is obtained.

I.R. (nujol): ν = 1762.1588 cm$^{-1}$
$^1$H—N.M.R. (60MHz, CDCl$_3$/TMSint)

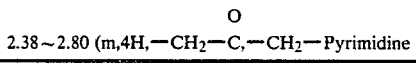

-continued

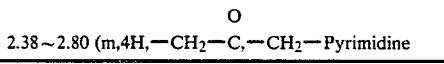

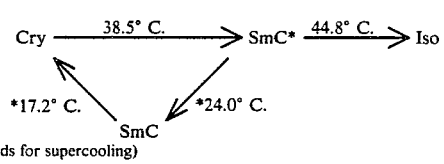

The transformation temperature of this liquid crystal compound is as follows.

Cry ⟶(38.5° C.) SmC* ⟶(44.8° C.) Iso
        ↖(*17.2° C.)      ↙(*24.0° C.)
                SmC
(* stands for supercooling)

This liquid crystal compound is sandwiched between PVA rubbing one-axis orientation processed plates, and the liquid crystal layer is fixed at a thickness of 2.5 μm, ±20 V voltage applied, then measured the characteristic under orthogonal nicol condition. The measuring temperature was 35° C.
Contrast (T on/T off): 11.5
Response speed: 3 ms

EXAMPLES 33 TO 38

The object compounds were obtained by means of operations similar to Example 1, utilizing the below mentioned optically active alkyl acid halide and alkyl pyrimidine phenol, as follows.

TABLE 2

| starting material | | | | object compound | | |
|---|---|---|---|---|---|---|
| $CH_3CH_2CH(CH_2)_mCOCl$ (with CH₃ and * on asymmetric carbon) | HO-⟨phenyl⟩-⟨pyrimidine⟩-$C_nH_{2n+1}$ | | | $CH_3CH_2CH(CH_2)_m$-COO-⟨phenyl⟩-⟨pyrimidine⟩-$C_nH_{2n+1}$ (with CH₃ and * on asymmetric carbon) | | |
| m | n | yield (%) | m, n | I.R. (nujol) $\nu$ (cm⁻¹) | H-N.M.R. (COCl₃/TMSint) $\delta$ (ppm) | |
| 2  $CH_3CH_2CH(CH_2)_2COCl$ (CH₃, *) | 8 | 69 | m = 2, n = 8 | 1760, 1585 | 8.56 (S,2H,Pyrimidine H); 8.45 (d,2H,Aromatic H); 7.18 (d,2H,Aromatic H); 2.37∼2.88 (m,4H, —CH₂—CO—, —CH₂—Pyrimidine) | |
| 0  $CH_3CH_2CHCOCl$ (CH₃, *) | 11 | 67 | m = 0, n = 11 | 1758, 1585 | 8.58 (S,2H,Pyrimidine H); 8.45 (d,2H,Aromatic H); 7.16 (d,2H,Aromatic H); 2.5∼2.90 (m,3H, —CH—CO—, —CH₂—Pyrimidine) CH₃; 1.29 (d,3H, CH—CO); 1.04 (t,3H, —CH₂—CH₃) | |
| 2  $CH_3CH_2CH(CH_2)_2COCl$ (CH₃, *) | 11 | 65 | m = 2, n = 11 | 1760, 1585 | 8.56 (S,2H,Pyrimidine H); 8.42 (d,2H,Aromatic H); 7.16 (d,2H,Aromatic H); 2.40∼2.85 (m,4H, —CH₂—CO—, —CH₂—Pyrimidine) | |
| 4  $CH_3CH_2CH(CH_2)_4COCl$ (CH₃, *) | 11 | 89 | m = 4, n = 11 | 1755, 1590 | 8.62 (S,2H,Pyrimidine H); 8.48 (d,2H,Aromatic H); 7.22 (d,2H,Aromatic H); 2.35∼2.90 (m,4H, —CH₂—CO—, —CH₂—Pyrimidine) | |
| 2  $CH_3CH_2CH(CH_2)_2COCl$ (CH₃, *) | 14 | 51 | m = 2, n = 14 | 1758, 1584 | 8.57 (S,2H,Pyrimidine H); 8.45 (d,2H,Aromatic H); 7.17 (d,2H,Aromatic H); 2.35∼2.80 (m,4H, —CH₂—CO—, —CH₂—Pyrimidine) | |
| 4  $CH_3CH_2CH(CH_2)_4COCl$ | 14 | 61 | m = 4, n = 14 | 1755, 1584 | 8.57 (S,2H,Pyrimidine H); 8.42 (d,2H,Aromatic H); 7.12 (d,2H,Aromatic H); 2.30∼2.72 (m,4H, —CH₂CO—, —CH₂—Pyrimidine) | |

The transition temperature and the response speed of these liquid crystals, measured in the similar way to example 1 is shown in the following table.

(s)-5-n-octyl-2-[4-(1-hydroxy-6-methyloctanoyl)-phenyl]pyrimidine 0.64 g is obtained.

$$\underset{*}{C_2H_5\overset{CH_3}{\underset{|}{CH}}(CH_2)_mCOO} - \phenyl - \pyrimidyl - C_nH_{2n+1}-n$$

| m | n | transition temperature (°C.) | response speed (measured temperature) |
|---|---|---|---|
| 2 | 8 | Cry $\underset{*49}{\overset{54.2}{\rightleftarrows}}$ Iso | — |
| 0 | 11 | Cry $\xrightarrow{52.2}$ Iso ; * Sm X $\overset{*}{\underset{40.7}{\nearrow}}$ | — |
| 2 | 11 | Cry $\xrightarrow{38.1}$ Sm C $\xrightarrow{*50.2}$ Iso ; $\underset{*\,Sm\,X}{\overset{8.2}{\swarrow}\!\!\!\nearrow\!29.0}$ | 28.5 μs (32.0° C.) |
| 4 | 11 | Cry $\xrightarrow{62.3}$ Iso ; $\underset{*\,Sm\,X}{\overset{41.2}{\swarrow}}\xleftarrow{*46.5}$ Sm C $\overset{*}{\underset{60.0}{\nearrow}}$ | 350 μs (56.7 °C.) |
| 2 | 14 | Cry $\longrightarrow$ Sm X $\underset{*36.4}{\overset{41.2}{\rightleftarrows}}$ Sm C $\xrightarrow{*53.1}$ Iso ; $\underset{*\,Sm\,Y}{\overset{13.9}{\swarrow}\!\!\!\nearrow\!23.0}$ | 350 μs (36.7°C.) |
| 4 | 14 | Cry $\underset{*}{\overset{46.0}{\rightleftarrows}}$ Sm X $\underset{50.0}{\overset{48.6}{\rightleftarrows}}$ Sm C $\xrightarrow{*62.8}$ Iso | 260 μs (50.2° C.) |

Here, Sm X and SmY stand for the Smectic phases except for the Sm A phase and the Sm C* phase; because it is not specifiable, we noted it as Sm X, Sm Y. * stands for supercooling.

As shown in the above table, with a liquid crystal of m=2, n=8, and a liquid crystal wherein m=0, n=11, the response speed cannot be measured because they do not have a Sm C* phase, but from various blend experiments, it has been determined that they can be utilized as an additive to speed up the response speed.

EXAMPLE 39

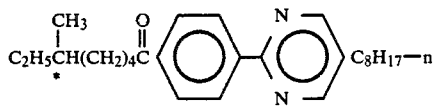

(1) Synthesis of (s)-5-n-octyl-2-[4-(1-hydroxy-6-methyloctanoyl)phenyl]pyrimidine.

Combine 0.82 g of (s)-4-(1-hydroxy-6-methyloctyl)-benzamidine hydrochloric acid salt, and 0.56 g of β-n-octyl-α-dimethylamino acrolein, after resolving in 20 ml dry ethanol, add 2.04 g 28% sodium methylate methanol solution, and allow the reaction to proceed for 13 hours under reflux. After the reaction, pour it into ice water and add hydrochloric acid, and then extract the reaction product with ethyl acetate. The ethyl acetate layer is washed with water and saturated salt water, dried, then filtered and the solvent removed. The obtained impure product is refined with silica gel chromatography and recrystallization, then optically active

| IR ν max cm$^{-1}$: | 3260, 1595, 1555 1440, 800 |
|---|---|
| $^1$H—NMR (60MHz, CDCl$_3$) δ (ppm): | 8.67 (S, 2H) 8.45 (d, 2H) 7.50 (d, 2H) 4.77 (t, 1H) 2.2~2.8 (m,) |

(2) Synthesis of (s)-5-n-octyl-2-[4-(6-methyloctanoyl)-phenyl]pyrimidine.

Combine 0.107 g of pyrimidinium bichromate with 5 ml of dried N,N-dimethylformamide. Next, slowly drip 0.08 g of (s)-5-n-octyl-2-[4-(1-hydroxy-6-methyloctyl)-phenyl]pyrimidine dissolved in 2 ml dried N,N-dimethylformamide 2 ml at room temperature.

When the dripping finishes, the reaction is allowed to continue for 2 hours at room temperature. After the reaction, add ether, to dilute it, then filter and separate the unsoluble matter, utilizing a high-flow-super-cell, the conduct an ether extraction of the reacted product. The ether layer is washed with dilute hydrochloric acid and water, dried filtered and the solvent removed. The resultant impure product is purified by silica gel chromatography and recrystallization, and 0.028 g of (s)-5-n-octyl-2-[4-(6-methyloctanoyl)phenyl]pyrimidine is obtained.

| IR ν max cm$^{-1}$: | 1680, 1610, 1580, 1545 |
|---|---|
| $^1$H—NMR (60MHz, CDCl$_3$) δ (ppm): | 0.6~2.2 (m, 30H) |

| | |
|---|---|
| 2.64 | (t, 2H) |
| 3.01 | (d, 2H) |
| 8.07 | (d, 2H) |
| 8.55 | (d, 2H) |
| 8.66 | (S, 2H) |

The phase transition temperature of this liquid crystal compound is as follows;

$$Cry \underset{*51}{\overset{67}{\rightleftarrows}} SmC^* \xrightarrow{69} SmA \xrightarrow{79.3} Iso$$

Furthermore, this liquid crystal compound is sandwiched between PVA rubbing one-axis orientation processed plates, the liquid crystal layer is fixed at a thickness of 2.5 μm, ±20 V voltage applied, and the response at orthogonal nicol measured, with the result that the value became 200 us, at 61° C.

EXAMPLE 40

$$\underset{C_2H_5CH(CH_2)_2O}{\overset{Cl}{|}} - \text{phenyl-pyrimidine} - C_8H_{17}-n$$

Synthesis of optically active (s)-5-n-octyl-2-[4-(3'chloropentyloxy)phenyl]pyrimidine Pour 0.77 g of sodium hydride (about 50% oil suspension) and 3 ml of dry N,N-dimethyl formamide into 10 ml two-mouth flask equipped with a dripping funnel, cooling tube and calcium chloride tube. Then drip 0.38 g of 4-(5-n-octyl-2-pyrimidinyl)phenol dissolved in 1 ml of dry N,N-dimethylformamide, into the flask at a temperature below the freezing point. After reaction for 30 minutes at room temperature, drip 0.37 g of optically active (s)-3-chloropentyl p-toluenesulfonic acid ester; this compound was synthesized by the general method with L(+)-3-hydroxyvaleric acid methyl ester [[α]$_D^{20}$=+28.1, (C=1, CHCl$_3$)] which is dissolved into 1 ml dry N,N-dimethylformamide.

When the dripping finishes, the reaction is allowed to continue for 8 hours using an 100° C. at oil bath. After the reaction, dry it, pour it into ice water, and extract it with ethyl acetate. The ethyl acetate layer is washed with 5% NaOH and water, dried, and the organic solvent filtered, and removed. The remaining oil-like is purified by means of a silica gel column chromatography, and repeatedly refined by recrystallization; 0.19 g of optically active (s)-5-n-octyl-2-[4-(3'-chloropentyloxy)phenyl]pyrimidine is obtained.

IR $v_{max}^{film}$(cm$^{-1}$) 1610, 1585, 1430, 1250, 1170, 1110, 800, 750

$^1$H—NMR (60MHz, CDCl$_3$/TMS int)

| δ (ppm): | | |
|---|---|---|
| | 8.62 | (S, 2H, Pyrimidine H) |
| | 8.42 | (d, 2H, Aromatic H) |
| | 7.02 | (d, 2H, Aromatic H) |
| | 4.03 | (t, 2H, —CH$_2$—O—) |
| | 2.60 | (t, 2H, —CH$_2$—pyr) |

The transition temperature!

$$Cry \underset{*13.5}{\overset{15.0}{\rightleftarrows}} SmA \xrightarrow{42.6} Iso$$

(here, * shows supercooling)

The compound of this example $$\underset{C_2H_5CH(CH_2)_2O}{\overset{Cl}{|}} - \text{phenyl-pyrimidine} - C_8H_{17}-n$$

does not have the Sm C* phase, so we measured the transition temperature and the response speed of the liquid crystal compound obtained by blending the above compound and the compound of Example 1.

$$\underset{C_2H_5CH(CH_2)_5O}{\overset{CH_3}{|}} - \text{phenyl-pyrimidine} - C_8H_{17}-n$$

in a proportion of 1:3.

The transition temperatures:

$$Cry \underset{*3°C.}{\overset{10.5}{\rightleftarrows}} SmC^* \xrightarrow{27.2} SmA \xrightarrow{51.7} Iso$$

The response speed: 220 μs (25° C.)

As it is obvious from comparison with the data of Example 1, the liquid crystal compound of this example has a faster response speed.

EXAMPLE 41

$$\underset{C_2H_5CH(CH_2)_2O}{\overset{CN}{|}} - \text{phenyl-pyrimidine} - C_{11}H_{23}-n$$

Synthesis of optically active (s)-5-n-undecyl-2-[4-(3'-cyanopentyloxy-phenyl]pyrimidine (1) Method of synthesis of optically active (s)-5-n-undecyl-2-[4-(3'-methanesulfonyloxy-pentyloxy)-phenyl]pyrimidine.

Dissolve 2.5 g of optically active (s)-5-n-undecyl-2-[4-(3'-hydroxy-pentyloxy)phenyl]pyrimidine in 25 ml dry pyridine. Slowly drip 0.76 g of methanesulfonyl chloride into this solution at −5° C. when dripping is complete, the reaction is continued for 2 more hours, dried, then allowed to react for another 2 hours at room temperature. After the reaction, pour it into ice water, and extract with ether. The ether layer is washed with dilute hydrochloric acid and water, dried and evaporated to remove the ether; an oil-like product is obtained. The oil-like product is crystallized and separated, and 2.63 g of optically active (s)-5-n-undecyl-2-[4-(3'-methanesulfonyloxypentyloxy)phenyl]pyrimidine is obtained.

I.R. $v_{max}^{nujol}$ (cm$^{-1}$): 1610, 1590, 1435, 1337,

-continued 1183, 1173, 910, 800

(2) Method of synthesis of optically active (s)-5-n-undecyl-2-[4-(3'-cyanopentyloxy)phenyl]pyrimidine.

Pour 2.63 g of optically active (s)-5-n-undecyl-2-[4-(3'-methanesulfonyloxy-pentyloxy)phenyl]pyrimidine obtained by means of method (1), and 10 ml of dry dimethyl sulfoxide into a 30 ml flask equipped with a cooling tube and calcium chloride tube, then after it is dissolved, add 0.32 g of sodium cyanide into it, and agitate it for 15 hours at 80° to 90° C., leave it to cool down, pour it into ice water, then ether extract to the reaction matter. The ether layer is washed with dilute hydrochloric acid and water, dried, the ether is evaporated and removed, and oil-like matter is obtained. This oil-like matter is crystallized and separated, and then 2.63 g of optically active (s)-5-n-undecyl-2-[4-(3'-methanesulfonyloxypentyloxy-pentyl oxy)phenyl]pyrimidine is obtained.

The specific rotatory power is $[\alpha]_D^{25} = -28.57°$ C. (C=2, CHCl$_3$), but the optical purity has not been studied enough.

| I.R $v_{max}^{nujol}$ (cm$^{-1}$): | 2240, 1605, 1585, 1430, 1245, 1165, 797 |
|---|---|
| $^1$H—NMR (60MHz, CDCl$_3$/TMS int) | |
| δ (ppm): | 8.60 (S, 2H, Pyrimidine H) |
| | 8.40 (d, 2H, Aromatic H) |
| | 7.00 (d, 2H, Aromatic H) |
| | 4.20 (t, 2H, —CH$_2$—O—) |
| | 0.65~3.15 (m, 31H) |

We measured the transition temperature of the obtained compound, and we obtained the following result.
The transition temperature:

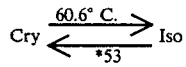

(wherein * shows supercooling).
As the compound of this example

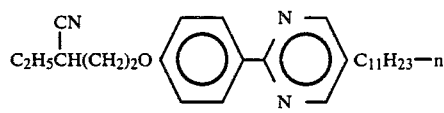

does not have the Sm C* phase, we measured the transition temperature and the response speed of the liquid crystal compound obtained by blending the above compound with the compound of Example 1

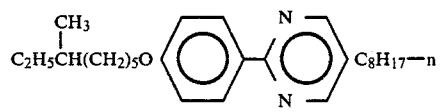

at a portion of 1:3.
The transition temperature:

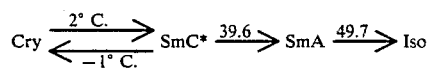

The response speed: 180 μs (30.0° C.).

As obvious from the comparison with the data of Example 1, it is understood that the liquid crystal compound of this example has a faster response speed without greatly changing the transition temperature.

EXAMPLE 42

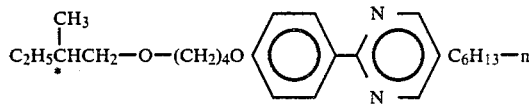

(1) Method of synthesis of optically active (s)-alkoxy alcohol (common to all the examples)

By having active amyl alcohol ($[\alpha]_D^{25} = -4.48°$ (neat)) as starting material and by reacting with appropriate diole in the general method, the following composition can be obtained.

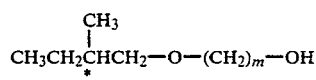

The optically active alkoxy alcohol obtained as above, can easily be changed to an alphatic or aromatic sulfonic acid ester or into to a halide.

(2) Method of synthesis of optically active (s)-5-n-hexyl-2-[4-(2-methylbutyloxy]phenyl]pyrimidine.

Pour 16 ml of dry N,N-dimethyl formamide and 0.29 g of sodium hydride (about 50% oil suspension), into a 100 ml four-mouth flask equipped with cooling tube, dropping funnel, thermometer, and calcium chloride tube. Next, drip 1.61 g of 4-(5-n-hexyl-2-pyrimidinyl)-phenol dissolved in 4 ml of dry N,N-dimethylformamide, allow it react until the hydrogen stops generating, then drip 2.0 g of optically active (s)-p-toluenesulfonic acid 2-methylbutyloxybutyl ester (this compound is obtained from the active amyl alcohol obtained according to the above method (1)) into the mixture and react for 7 hours at 70° to 80° C. After the reaction, it is poured into ice water, and the product is extracted with chloroform.

The chloroform layer is water-washed and dried, and the chloroform is evaporated and removed. The obtained impure product is repeatedly refined, and 1.2 g of optically active (s)-5-n-hexyl-2-[4-(2'-methylbutyloxybutyloxy).phenyl]pyrimidine is obtained.

| I.R. $v_{max}^{film}$(cm$^{-1}$): | 1610, 1585, 1425, 1250, 1170, 1110, 800 |
|---|---|
| $^1$H—NMR (60 MHz, CDCl$_3$/TMS int) δ (ppm): | 8.52 (S, 2H, Pyrimidine H) |
| | 8.36 (d, 2H, Aromatic H) |
| | 6.94 (d, 2H, Aromatic H) |
| | 3.97 (t, 2H, —CH$_2$—O—) |
| | 3.39 (t, 2H, —CH$_2$—O—) |
| | 3.18 (dd, 2H, —CH—CH$_2$—O—) |
| | 2.50 (t, 2H, —CH$_2$—pyr) |
| | 0.5~2.2 (m, 24H) |

The following result were obtained by measuring the transition temperature (0° C.) of this compound.

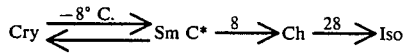

EXAMPLE 43

We synthesized optically active (s)-5-n-octyl-2-[4-(2'-methylbutyloxybutyloxy)phenyl]pyrimidine with a method similar to that of Example 42.

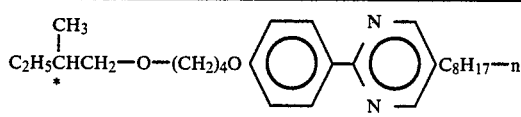

I.R. $\nu_{max}^{film}$ = :1610, 1585, 1430, 1250, 1170, 1110, 800
$^1$H—NMR (60MHz, CDCl$_3$/TMS int)
δ(ppm): 8.50 (S, 2H, Pyrimidine H)
8.40 (d, 2H, Aromatic H)
6.99 (d, 2H, Aromatic H)

4.05 (t, 2H, —CH$_2$—O—)

3.46 (t, 2H, —CH$_2$—O—)

3.24 (dd, 2H, —CH—CH$_2$—O—)

2.58 (t, 2H, —CH$_2$—pyr)

0.5~2.1 (m, 28H)

The following results were obtained by measuring the transition temperature (°C.) of the obtained compound.

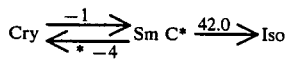

EXAMPLE 44

We synthesized optically active (s)-5-n-undecyl-2-[4-(2'-methylbutyloxybutyloxy)phenyl]pyrimidine with a method similar to that of Example 42.

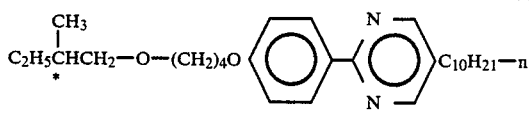

I.R. $\nu_{max}^{film}$ = :1610, 1585, 1435, 1260, 1175, 1115, 800
$^1$H—NMR (60MHz, CDCl$_3$/TMS int)
δ(ppm): 8.57 (S, 2H, Pyrimidine H)
8.36 (d, 2H, Aromatic H)
6.98 (d, 2H, Aromatic H)

4.02 (t, 2H, —CH$_2$—O—)

3.42 (t, 2H, —CH$_2$—O—)

3.20 (dd, 2H, —CH—CH$_2$—O—)

2.55 (t, 2H, —CH$_2$—pyr)

0.5~2.1 (m, 34H)

The following results were obtained by measuring the transition temperature (°C.) of this compound.

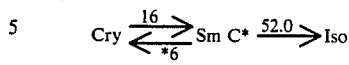

EXAMPLE 45

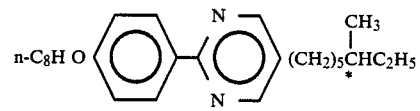

Method of synthesis of optically active (s)-2-[4-n-octyloxyphenyl]-5-[6-methyloctyl]pyrimidine Pour 0.33 g of sodium hydride (about 50% oil suspension), 3 ml of dry N,N-dimethylformamide into a 30 ml three-mouth flask equipped with a cooling tube, thermometer, dripping funnel, and calcium chloride tube. Next, slowly drip 1.71 g of optically active (s)-4-[5-(6-methyl octyl)-2-pyrimidinyl]phenol which is dissolved in 6 ml of dry N,N-dimethylformamide, into the flask at room temperature. Furthermore, after reacting it for 30 minutes, add 1.10 g of 1-bromoctane, allow to react for 7 hours at 90° C. After the reaction, pour the mixture into ice water, then extract the product with ethyl acetate. The organic layer is thoroughly washed with water, dried, the organic solvent is evaporated and removed, and then the impure product is obtained. This impure product is refined with silica gel chromatography, and recrystallized to obtain 1.3 g of optically active (s)-2-[4-n-octyloxyphenyl]-5-[6-methyloctyl]-pyrimidine.

I.R $\nu$max (cm$^{-1}$): 1610, 1585, 1430, 1250 1170, 800
$^1$H—NMR (60MHz, CDCl$_3$)
δ(ppm): 8.38 (S, 2H)
8.28 (d, 2H)
6.97 (d, 2H)
3.27~4.20 (m, 4H)
0.6~2.1 (m, 32H)

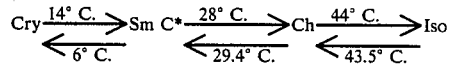

EXAMPLE 46

Method of synthesis of (s)-2-(4-n-octylphenyl)-5-(6-methyloctyloxy)pyrimidine

Pour 2.64 g of 4-n-octylbenzamidine hydrochloric acid salt, 2.38 g of (s)-α-(6-methyl octyloxy)-β-(dimethylamino)acrolein, and 20 ml ethanol anhydride into a three-mouth flask equipped with a cooling tube, calcium chloride tube, dripping funnel, and thermometer. Next, slowly drip 4.18 g of 28% sodium methylate.methanol solution into the flask, at room temperature. After the dripping, and refluxing, we examined the reaction for 11 hours. When the reaction finishes, pour it into ice water, and extract the reaction product with ethyl acetate. The ethyl acetate layer is water washed, dried, and the solvent is evaporated and removed at low pressure. The obtained impure product is refined with silica gel column chromatography, and recrystallized, and then 2.41 g of (s)-2-[4-n-octylphenyl)-5-(6-methyloctyloxy)pyrimidine is obtained.

I.R νmax (cm$^{-1}$): 1610, 1578, 1440 1280, 785
$^1$H—NMR (60MHz, CDCl$_3$)
δ(ppm): 0.65~2.2 (m, 32H)
2.66 (t, 2H)
4.04 (t, 2H)
7.30 (d, 2H)
8.30 (d, 2H)
8.45 (s, 2H)

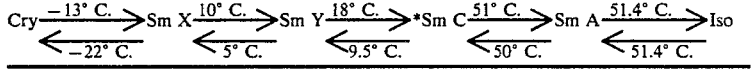

Here, Sm X and Sm Y are smectic phases, which phases are unconfirmed.

EXAMPLE 47

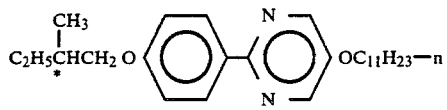

Method of synthesis of
(s)-5-(n-undecyloxy)-2-[4-(2-methylbutyloxy)phenyl]-pyrimidine Suspend 0.185 g of 50% sodium hydride in 2 ml of dry DMF, slowly drip 1.1 g of 2-(4-hydroxyphenyl)-5-(n-undecyl)pyrimidine which is resolved in 5 ml of dry DMF at a temperature below freezing point into the mixture, agitate for 30 minutes at room temperature, and then drip 0.785 g of 2-methyl-1-(p-trisulfonoxy)-butane (this is regulated by (s)-amyl alcohol ([α]$_D^{23}$ −5.8° (neat)). Next, after agitating the reaction solution for 5 hours at 100° C., pour it into ice water, and extract the reaction product with ethyl acetate.

The ethyl acetate layer is washed with 5% NaOH, dried with magnesium sulfate, the remaining sediment is purified by evaporating and removing the solvent, with silica gel column chromatography and recrystallization to obtain (s)-5-n-(n-undecyloxy)-2-[4-(2-methylbutyloxy)phenyl]pyrimidine, at yield of 76%.

EXAMPLE 48 TO 50

With the compound shown in the following general formula, we synthesized a compound where we changed m and n by a method similar to that of Example 47.

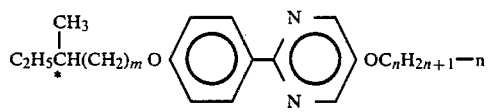

The characteristics of these compounds are all shown in the following table with Example 47.

TABLE 4

| object compound | Characteristic values of the compounds | | |
|---|---|---|---|
| | IR τ max cm$^{-1}$ | $^1$H—NMR | |
| example 47 m = 1 n = 11 | 1615, 1590, 1550, 1525, 1445, 1250 | 0.7~2.2 3.85 4.04 7.00 | (m, 30H) (d, 2H) (t, 2H) (d, 2H) |

TABLE 4-continued

| object compound | Characteristic values of the compounds | | |
|---|---|---|---|
| | IR τ max cm$^{-1}$ | $^1$H—NMR | |
| | | 8.33 8.42 | (d, 2H) (s, 2H) |
| example 48 m = 2 n = 8 | 1612, 1585, 1555, 1512, 1440 | 0.7~2.1 4.05 6.95 8.28 8.36 | (m, 27H) (t, 4H) (d, 2H) (d, 2H) (s, 2H) |
| example 49 m = 5 n = 8 | 1610, 1584, 1525, 1515, 1435 | 0.6~2.1 2.60 4.00 6.97 8.36 8.57 | (m, 32H) (t, 2H) (t, 2H) (d, 2H) (d, 2H) (s, 2H) |
| example 50 m = 2 n = 11 | 1610, 1510, 1550, 1512, 1440 | 0.7~2.27 4.13 7.02 8.35 8.45 | (m, 32H) (t, 4H) (d, 2H) (d, 2H) (s, 2H) |

TABLE 5

The phase transition temperature and the response speed of the compound

| object compound | transition temperature | response speed |
|---|---|---|
| example 47 m = 1 n = 11 | Cry ⇌$_{*44}^{58}$ Sm C ⇌$^{*72.7}$ Sm A ⇌$^{76.7}$ Iso | τ = 290 μs (66° C.) |
| example 48 m = 2 n = 8 | Cry ⇌$_{*}^{52.4}$ Sm C ⇌$^{*73.1}$ Sm A ⇌$^{76.5}$ Iso | τ = 900 μs (65° C.) |
| example 49 m = 5 n = 8 | Cry ⇌$_{*}^{40.7}$ Sm C ⇌$^{*82.8}$ Sm A ⇌$^{89.1}$ Iso | τ = 1.5 ms (43° C.) |
| example 50 m = 2 n = 11 | Cry ⇌$_{*32.3}^{48.5}$ Sm C ⇌$^{*78.0}$ Iso | τ = 310 μs (70° C.) |

(here, *stands for supercooling)

EXAMPLE 51

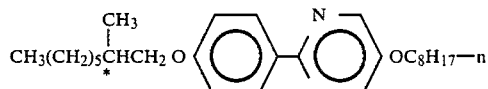

We synthesized (s)-5-(n-octyloxy)-2-[4-(2-methyloctyl)phenyl]pyrimidine by means of a method similar to that of Example 47.

The response speed, determined by a method similar to that of the transition temperature, is shown as follows.

Transition temperature:

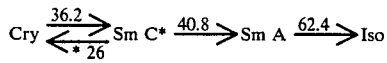

Response speed: 300 μs (30° C.).

EXAMPLE 52

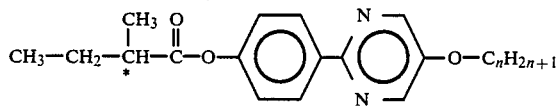

wherein n=11, * shows an asymmetric carbon atom and m, with reference to the general formula, is 0.

Method of synthesis of (s)-5-n-undecyloxy-2-[4-(2-methylbutanoyloxy)phenyl]-pyrimidine Pour 0.328 g of 2-methylbutanoic acid synthesized from (s)-amylalcohol ($[\alpha]_D^{23}$ −5.8° (neat)), 1.1 g of 4-(5-n-undecyloxy-2-pyrimidinyl)phenol, 8 ml of anhydrous chloroform and 0.662 g of 4-dimethylaminopyridine, S,S'-dicyclohexylcarbodimide into a 25 ml flask and allow to react for one whole day at room temperature. After the reaction, filter and separate the insoluble matters, and extract the reaction product with chloroform. The organic layer is washed with water, 2N hydrochloric acid and water, dried and evaporated to remove the organic solvent. The reaction product is purified with silica gel chromatography and re-crystallized crystal, and then optically active (s)-5-n-undecyloxy-2-[4-(2-methylbutanoyloxy)phenyl]pyrimidine is obtained at a yield of 70%.

| I.R $\nu_{max}^{nujol}$ (cm$^{-1}$): | 1762, 1602, 1550, 1440, 1278, |
|---|---|
| $^1$H—NMR (60MHz, CDCl$_3$) | |
| δ (ppm): | 8.42 (S, 2H) |
| | 8.40 (d, 2H) |
| | 7.17 (d, 2H) |
| | 4.40 (t, 2H) |
| | 2.3~2.8 (m, 1H) |
| | 0.6~2.2 (m, 29H) |

EXAMPLES 53 TO 57

We obtained the object compounds with a operation similar to Example 1, utilizing the (s) alkylcarboxylic acid synthesized from the below mentioned (s) amyl alcohol$[\alpha]_D^{-23}$ −5.8° (neat), and alkyloxypyrimidinyphenol.

Refer to the following Table 6.

TABLE 6

| example | starting material $CH_3CH_2CH(CH_2)_m COOH$ (with * on CH) | m | starting material (phenol-pyrimidine) $O-C_nH_{2n+1}$ | n | yield (%) | object compound $CH_3CH_2CH(CH_2)_mCOO$— (with * on CH), m | n | I.R. ν nujol max (cm$^{-1}$) | H—N.M.R. (60MHz, CDCl$_3$) δ (ppm) |
|---|---|---|---|---|---|---|---|---|---|
| 53 | $CH_3CH_2CH\ COOH$ | 0 | HO—⌬—pyrimidine—O—C$_8$H$_{17}$ | 8 | 60 | m = 0 | n = 8 | 1760, 1555, 1440, 1290, 1205, 1160 | 8.47 (S,2H); 8.37 (d,2H); 7.17 (d,2H); 4.17 (t,2H); 2.35~3.04 (m,1H); 0.77~2.35 (m,23H) |
| 54 | $CH_3CH_2CH—CH_2COOH$ | 1 | HO—⌬—pyrimidine—O—C$_8$H$_{17}$ | 8 | 77 | m = 1 | n = 8 | 1762, 1598, 1560, 1450, 1290 | 8.41 (S,2H); 8.36 (d,2H); 7.16 (d,2H); 4.08 (t,2H); 2.31~2.85 (m,2H); 0.7~2.25 (m,24H) |
| 55 | $CH_3CH_2CH(CH_2)_2 COOH$ | 2 | HO—⌬—pyrimidine—O—C$_8$H$_{17}$ | 8 | 66 | m = 2 | n = 8 | 1762, 1598, 1560, 1450, 1290 | 8.43 (S,2H); 8.42 (d,2H); 7.21 (d,2H); 4.05 (t,2H); 2.58 (t,2H); 0.6~2.1 (m,30H) |
| 56 | $CH_3CH_2CH(CH_2)_4 COOH$ | 4 | HO—⌬—pyrimidine—O—C$_8$H$_{17}$ | 8 | 75 | m = 4 | n = 8 | 1762, 1598, 1560 | 8.44 (S,2H); 8.40 (d,2H); 7.19 (d,2H); 4.06 (t,2H); 2.58 (t,2H); 0.65~2.15 (m,30H) |
| 57 | $CH_3CH_2CH—CH_2 COOH$ | 1 | HO—⌬—pyrimidine—O—C$_{11}$H$_{23}$ | 11 | 66 | m = 1 | n = 11 | 1760, 1598, 1560, 1450, 1290 | 8.42 (S,2H); 8.35 (d,2H); 7.27 (d,2H); 4.08 (t,2H); 2.32~2.82 (m,2H); 0.68~2.27 (m,30H) |

TABLE 7

The transition temperature and the response speed of the compounds

| object compound | phase transition temperature | response speed |
|---|---|---|
| example 52<br>m = 0<br>n = 11 | Cry $\underset{*42}{\overset{43}{\rightleftarrows}}$ Sm C $\xrightarrow{*64.1}$ Sm A $\xrightarrow{67.2}$ Iso | τ = 230 μs (60° C.) |
| example 53<br>m = 0<br>n = 8 | Cry $\underset{56.2}{\overset{66.0}{\rightleftarrows}}$ Iso ; Sm C $\xrightarrow{62.2}$ * | τ = 150 μs (62° C.) |
| example 54<br>m = 1<br>n = 8 | Cry $\underset{*59.8}{\overset{70}{\rightleftarrows}}$ Sm C $\xrightarrow{*72.2}$ Sm A $\xrightarrow{72.9}$ Iso | τ = 250 μs (66° C.) |
| example 55<br>m = 2<br>n = 8 | Cry $\underset{70.2}{\overset{78.0}{\rightleftarrows}}$ Iso ; Sm C $\xrightarrow{75.5}$ * | — |
| example 56<br>m = 4<br>n = 8 | Cry $\underset{*64.7}{\overset{76.0}{\rightleftarrows}}$ Sm C $\xrightarrow{*79.5}$ Iso | τ = 1.3 ms (78° C.) |
| example 57<br>m = 1<br>n = 11 | Cry $\xrightarrow{54.8}$ Sm C $\xrightarrow{*72.3}$ Sm A $\xrightarrow{77.8}$ Iso ; S$_2$ $\underset{33.7}{\rightleftarrows}$ S$_1$ | τ = 240 μs (60° C.) |

*shows supercooling

EXAMPLES 58 TO 61

The the structural formula and the transition temperature of synthesized specific compounds are shown in the following Table 8.

TABLE 8

| example No. | structural formula | phase transition temperature (°C.) |
|---|---|---|
| 58 | C$_2$H$_5$CH(CH$_2$)$_5$O–⟨phenyl⟩–⟨pyrimidine⟩–COC$_8$H$_{17}$–n, with CH$_3$ branch on * carbon | Cry $\underset{*}{\overset{78.5}{\rightleftarrows}}$ Sm C $\xrightarrow{*79.7}$ Iso |
| 59 | n-C$_8$H$_{17}$O–⟨phenyl⟩–⟨pyrimidine⟩–CO(CH$_2$)$_5$CHC$_2$H$_5$ with CH$_3$ branch | Cry $\underset{*}{\overset{79.9}{\rightleftarrows}}$ Sm C $\xrightarrow{*80.7}$ Iso |
| 60 | n-C$_{11}$H$_{23}$O–⟨phenyl⟩–⟨pyrimidine⟩–OCH$_2$CHC$_2$H$_5$ with CH$_3$ branch | Cry $\underset{*41.0}{\overset{51.0}{\rightleftarrows}}$ Iso |
| 61 | n-C$_{10}$H$_{21}$CO–⟨phenyl⟩–⟨pyrimidine⟩–OCH$_2$CHC$_2$H$_5$ with CH$_3$ branch | Cry $\underset{*51.0}{\overset{58.2}{\rightleftarrows}}$ Iso |

EXAMPLE 62

Method of synthesis of (R)-5-n-undecyl-2-[4-(2'-methyl butyloxy)phenyl]pyrimidine Suspend 0.57 g of 50% sodium hydride in 6 ml of dried N,N-dimethylformamide, dissolve and add 3.2 g of 2-(4-hydroxyphenyl)-5-n-undecylpyrimidine to 6 ml of dry N,N-dimethylformamide, agitate it for 60 minutes at room temperature, dissolve and add 2.9 g (R)-2-methyl-1-(p-toluensulfonyl)oxybutane to 5 ml of dry N,N-dimethylformamide, heat the compound to 75° to 80° C., allow to react under agitation for 8 hours, pour the reacted solution into ice water, extract with ethyl acetate, wash with salt water, dry with magnesium sulfate, evaporate and remove the solvent; 4.27 g of sediment remains. Purify this with silica gel column chromatography and recrystallization and 2.0 g of (R)-5-n-undecyl-2-[4-(2'-methyl butyloxy)phenyl]pyrimidine are obtained.

$(\alpha)_D^{25}$ − 7.05 (C = 2.0, CHCl$_3$)
I.R ν max (cm$^{-1}$):  1610, 1590, 1435, 1255, -continued

| | |
|---|---|
| | 1170, 850, 800 |
| $^1$H—NMR (60MHz, CDCl$_3$) | |
| δ (ppm): | 0.6~2.23 (m, 30H) |
| | 2.53 (t, 2H) |
| | 3.72 (d, 2H) |
| | 6.88 (d, 2H) |
| | 8.24 (d, 2H) |
| | 8.43 (s, 2H) |

The transition temperature of this liquid crystal compound is as follows.

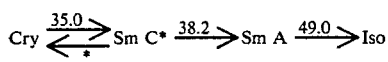

* shows supercooling.

This liquid crystal compound is sandwiched between PVA rubbing one-axis orientation processed plates, the liquid crystal layer thickness fixed at 2.5 μm, ±20 voltage applied, and the characteristic measured at orthogonal nicol. The measuring temperature is 35° C.

The response speed: 210 μs.

EXAMPLE 63

Method of synthesis of (R)-5-n-octyl-2-[4-(4'-methylhexyloxy)phenyl]pyrimidine

Suspend 0.605 g of 50% sodium hydride into 5 ml dry N,N-dimethylformamide, dissolve and add 3.0 g of 2-(4-hydroxyphenyl)-5-n-octyl pyrimidine in 7 ml of dry dimethyl formamide, agitate for 60 minutes at room temperature, dissolve and add 2.84 g of (R)-4-methyl-1-(p-toluenesulfonyl).oxyhexane to 5 ml. of dry N,N-dimethylformamide, heat the compound to 75° to 80° C., reaction to proceed under agitation for 8 hours, pour into ice water, extract with ethyl acetate, wash with salt water, dry with magnesium sulfate, evaporate and remove the solvent, and 4.15 g of sediment remains. Refine this sediment with silica gel column chromatography and recrystallization, and 2.5 g of (R)-5-n-octyl-2-[4-(4'-methylhexyloxy)phenyl]pyrimidine are obtained.

| | |
|---|---|
| $(\alpha)_D^{25}$ − 5.25 (C = 2, CHCl$_3$) | |
| I.R ν max (cm$^{-1}$): | 1610, 1590, 1435, 1255, 1170 |
| | 850, 802 |
| $^1$H—NMR (60MHz, CDCl$_3$) | |
| δ (ppm): | 0.6~2.20 (m, 28H) |
| | 2.55 (t, 2H) |
| | 3.97 (t, 2H) |
| | 6.91 (d, 2H) |
| | 8.25 (d, 2H) |
| | 8.48 (s, 2H) |

The transition temperature of this liquid crystal compound is as follows;

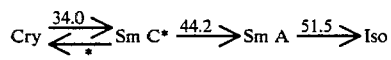

* shows supercooling.

This liquid crystal compound is sandwiched between PVA rubbing one-axis orientation processed plates, the liquid crystal layer fixed at a thickness of 2.5 μm, ±20 V of voltage applied, and the characteristics measured under orthogonal nicol. The measured temperature is 27° C.

The response speed is 245 μs.

UTILIZATION POSSIBILITY IN INDUSTRY

As shown in the above examples, the new liquid crystal compounds of the present invention have a very good response ability, and are compounds which hold the Sm C* phase over a wide temperature range close to room temperature, thus, resulting in liquid crystal compounds having a practical Sm C* phase temperature range; these are highly advantageous compositions which will contribute much to the practice of ferroelectric liquid crystal display.

We claim:

1. A ferroelectric liquid crystal compound of the formula

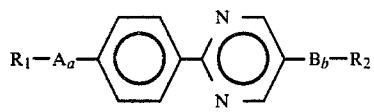

wherein one of R$_1$ and R$_2$ is a straight chain alkyl group of 5 to 14 carbon atoms and the other is an alkyl or alkoxyalkyl group which contains just one asymmetric carbon atom, each of a and b is 0 or 1, one member of the group —CH$_3$, —CN or —Cl is attached to the asymmetric carbon atom and each of A and B is —O—,

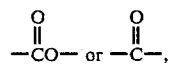

wherein:
when a is 0, B is —O— and b is 1;
when A is —O— and a is 1, B is —O— or

and b is 0 or 1;
when A is

and a is 1, B is —O— and b is 0 or 1, and when A is

and a is 1, b is 0.

2. A ferroelectric liquid crystal compound as claimed in claim 1, of the formula

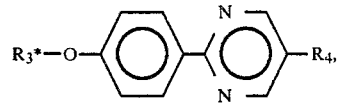

wherein R$_3$* is an alkyl group containing just one assymetric carbon atom and R$_4$ is a straight chain alkyl group.

3. A ferroelectric liquid crystal compound as claimed in claim 1, of the formula

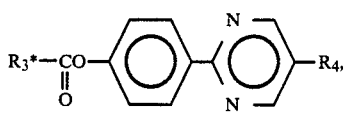

wherein R₃* is and alkyl group containing just one asymmetric carbon atom and R₄ is a straight chain alkyl group.

4. A ferroelectric liquid crystal compound as claimed in claim 1, of the formula

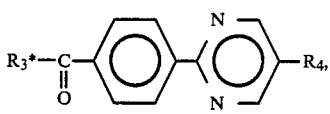

wherein R₃* is an alkyl group containing just one asymmetric carbon atom and R₄ is a straight chain alkyl group.

5. A ferroelectric liquid crystal compound as claimed in claim 1, of the formula

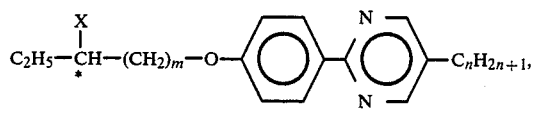

wherein m is 0 to 8, n is 5 to 14, X is —Cl or —CN and * shows an asymmetric carbon atom.

6. A ferroelectric liquid crystal compound as claimed in claim 1, of the formula

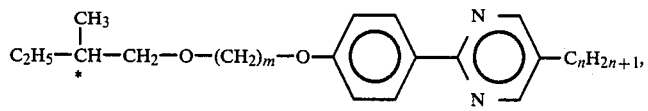

wherein m is 1 to 8, n is 5 to 14 and C shows the assymetric carbon atom.

7. A ferroelectric liquid crystal compound as claimed in claim 1, of the formula

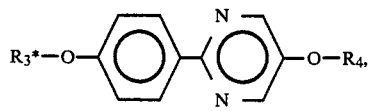

wherein R₃* is an alkyl group containing just one assymmetric carbon atom and R₄ is a straight chain alkyl group.

8. A ferroelectric liquid crystal compound as claimed in claim 1, of the formula

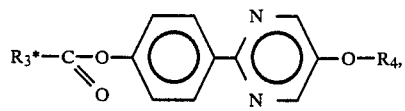

9. A ferroelectric liquid crystal compound as claimed in claim 1, of the formula

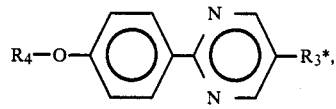

wherein R₃* is an alkyl group containing just one assymmetric carbon atom and R₄ is a stright chain alkyl group.

10. A ferroelectric liquid crystal compound as claimed in claim 1, of the formula

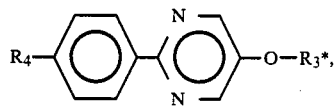

wherein R₃* is an alkyl group containing just one assymmetric carbon atom and R₄ is a striaght chain alkyl group.

11. A ferroelectric liquid crystal compound as claimed in claim 1, of the formula

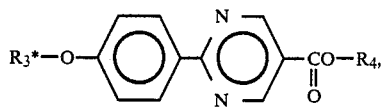

wherein R₃* is an alkyl group containing just one assymmetric carbon atom and R₄ is a straight chain alkyl group.

12. A ferroelectric liquid crystal compound as claimed in claim 1, of the formula

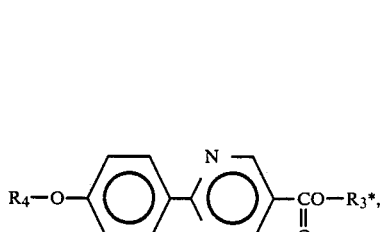

wherein R₃* is an alkyl group containing just one assymmetric carbon atom and R₄ is a straight chain alkyl group.

13. A ferroelectric liquid crystal compound as claimed in claim 1, of the formula

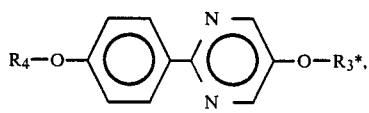

wherein R₃* is an alkyl group containing just one assymmetric carbon atom and R₄ is a straight chain alkyl group.

14. A ferroelectric liquid crystal compound as claimed in claim 1, of the formula

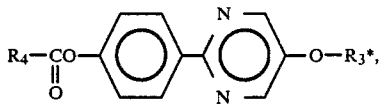

wherein R3* is an alkyl group containing just one assymmetric carbon atom and R4 is a straight chain alkyl group.

15. A ferroelectric liquid crystal compound as claimed in claim 1, wherein one of $R_1$ and $R_2$ is a straight chain alkyl group of 5 to 14 carbon atoms and the other is an alkoxyalkyl group containing just one asymmetric carbon atom which is located in the alkoxy portion of the alkoxyalkyl group.

16. The compound of claim 2, which is (s)-5-n-octyl-2-[4-(6'-methyloctyloxy)phenyl]pyrimidine.

17. The compound of claim 2, which is (s)-5-n-undecyl-2-[4-(2'-methylbutyloxy)phenyl]pyrimidine.

18. The compound of claim 2, which is (s)-5-n-hexyl-2-[4-(3'-methylpentyloxy)phenyl]pyrimidine.

19. The compound of claim 2, which is (s)-5-n-heptyl-2-[4-(3'-methylpentyloxy)phenyl]pyrimidine.

20. The compound of claim 2, which is (s)-5-n-octyl-2-[4-(3'-methylpentyloxy)phenyl]pyrimidine.

21. The compound of claim 2, which is (s)-5-n-nonyl-2-[4-(3'-methylpentyloxy)phenyl]pyrimidine.

22. The compound of claim 2, which is (s)-5-n-decyl-2-[4-(3'-methylpentyloxy)phenyl]pyrimidine.

23. The compound of claim 2, which is (s)-5-n-undecyl-2-[4-(3'-methylpentyloxy)phenyl]pyrimidine.

24. The compound of claim 2, which is (s)-5-n-dodecyl-2-[4-(3'-methylpentyloxy)phenyl]pyrimidine.

25. The compound of claim 2, which is (s)-5-n-hexyl-2-[4-(4'-methylhexyloxy)phenyl]pyrimidine.

26. The compound of claim 2, which is (s)-5-n-heptyl-2-[4-(4'-methylhexyloxy)phenyl]pyrimidine.

27. The compound of claim 2, which is (s)-5-n-octyl-2-[4-(4'-methylhexyloxy)phenyl]pyrimidine.

28. The compound of claim 2, which is (s)-5-n-nonyl-2-[4-(4'-methylhexyloxy)phenyl]pyrimidine.

29. The compound of claim 2, which is (s)-5-n-decyl-2-[4-(4'-methylhexyloxy)phenyl]pyrimidine.

30. The compound of claim 2, which is (s)-5-n-undecyl-2-[4-(4'-methylhexyloxy)phenyl]pyrimidine.

31. The compound of claim 2, which is (s)-5-n-dodecyl-2-[4-(4'-methylhexyloxgy)phenyl]pyrimidine.

32. The compound of claim 2, which is (s)-5-n-tetradecyl-2-[4-(4'-methylhexyloxy)phenyl]pyrimidine.

33. The compound of claim 2, which is (s)-5-n-hexyl-2-[4-(5'-methylheptyloxy)phenyl]pyrimidine.

34. The compound of claim 2, which is (s)-5-n-heptyl-2-[4-(5'-methylheptyloxy)phenyl]pyrimidine.

35. The compound of claim 2, which is (s)-5-n-octyl-2-[4-(5'-methylheptyloxy)phenyl]pyrimidine.

36. The compound of claim 2, which is (s)-5-n-nonyl-2-[4-(5'-methylheptyloxy)phenyl]pyrimidine.

37. The compound of claim 2, which is (s)-5-n-decyl-2-[4-(5'-methylheptyloxy)phenyl]pyrimidine.

38. The compound of claim 2, which is (s)-5-n-undecyl-2-[4-(5'-methylheptyloxy)phenyl]pyrimidine.

39. The compound of claim 2, which is (s)-5-n-dodecyl-2-[4-(5'-methylheptyloxy)phenyl]pyrimidine.

40. The compound of claim 2, which is (s)-5-n-hexyl-2-[4-(6'-methyloctyloxy)phenyl]pyrimidine.

41. The compound of claim 2, which is (s)-5-n-heptyl-2-[4-(6'-methyloctyloxy)phenyl]pyrimidine.

42. The compound of claim 2, which is (s)-5-n-nonyl-2-[4-(6'-methyloctyloxy)phenyl]pyrimidine.

43. The compound of claim 2, which is (s)-5-n-decyl-2-[4-(6'-methyloctyloxy)phenyl]pyrimidine.

44. The compound of claim 2, which is (s)-5-n-undecyl-2-[4-(6'-methyloctyloxy)phenyl]pyrimidine.

45. The compound of claim 2, which is (s)-5-n-dodecyl-2-[4-(6'-methyloctyloxy)phenyl]pyrimidine.

46. The compound of claim 2, which is (s)-5-n-tetradecyl-2-[4-(6'-methyloctyloxy)phenyl]pyrimidine.

47. The compound of claim 2, which is (R)-5-n-undecyl-2-[4-(2'-methylbutyloxy)phenyl]pyrimidine.

48. The compound of claim 2, which is (R)-5-n-octyl-2-[4-(4'-methylhexyloxy)phenyl]pyrimidine.

49. The compound of claim 3, which is (s)-5-n-octyl-2-[4-(6'-methyloctanoyloxy)phenyl]pyrimidine.

50. The compound of claim 3, which is (s)-5-n-octyl-2-[4-(4'-methylhexanoyloxy)phenyl]pyrimidine.

51. The compound of claim 3, which is (s)-5-n-undecyl-2-[4-(2'-methylbutanoyloxy)phenyl]pyrimidine.

52. The compound of claim 3, which is (s)-5-n-undecyl-2-[4-(4'-methylhexanoyloxy)phenyl]pyrimidine.

53. The compound of claim 3, which is (s)-5-n-undecyl-2-[4-(6'-methyloctanoyloxy)phenyl]pyrimidine.

54. The compound of claim 3, which is (s)-5-n-tetradecyl-2-[4-(4'-methylhexanoyloxy)phenyl]pyrimidine.

55. The compound of claim 3, which is (s)-5-n-tetradecyl-2-[4-(6'-methyloctanoyloxy)phenyl]pyrimidine.

56. The compound of claim 4, which is (s)-5-n-octyl-2-[4-(6'-methyloctanyloxy)phenyl]pyrimidine.

57. The compound of claim 5, which is (s)-5-n-octyl-2-[4-(3'-chloropentyloxy)phenyl]pyrimidine.

58. The compound of claim 5, which is (s)-5-n-undecyl-2-[4-(3'-cyanopentyloxy)phenyl]pyrimidine.

59. The compound of claim 6, which is (s)-5-n-hexyl-2-[4-(2'-methylbutyloxybutyloxy)phenyl]pyrimidine.

60. The compound of claim 6, which is (s)-5-n-octyl-2-[4-(2'-methylbutyloxybutyloxy)phenyl]pyrimidine.

61. The compound of claim 6, which is (s)-5-n-undecyl-2-[4-(2'-methylbutyloxybutyloxy)phenyl]pyrimidine.

62. The compound of claim 7, which is (s)-5-(n-undecyloxy)-2-[4-(2'-methylbutyloxy)phenyl]pyrimidine.

63. The compound of claim 7, which is (s)-5-(n-octyloxy)-2-[4-(3'-methylheptyloxy)phenyl]pyrimidine.

64. The compound of claim 7, which is (s)-5-(n-octyloxy)-2-[4-(6'-methyloctyloxy)phenyl]pyrimidine.

65. The compound of claim 7, which is (s)-5-(n-undecyloxy)-2-[4-(3'-methylheptyloxy)phenyl]pyrimidine.

66. The compound of claim 7, which is (s)-5-(n-undecyloxy)-2-[4-(2'-methyloctyloxy)phenyl]pyrimidine.

67. The compound of claim 8, which is (s)-5-(n-undecyloxy)-2-[4-(2'-methylbutanoyloxy)phenyl]pyrimidine.

68. The compound of claim 8, which is (s)-5-(n-octyloxy)-2-[4(2'-methylbutanoyloxy)phenyl]pyrimidine.

69. The compound of claim 8, which is (s)-5-(n-octyloxy)-2-[4-(3'-methylheptanoyloxy)phenyl]pyrimidine.

70. The compound of claim 8, which is (s)-5-(n-octyloxy)-2-[4-(4'-methylhexanoyloxy)phenyl]pyrimidine.

71. The compound of claim 8, which is (s)-5-(n-octyloxy)-2-[4-(6'-methyloctanoyloxy)phenyl]pyrimidine.

72. The compound of claim 8, which is (s)-5-(n-undecyloxy)-2-[4-(3'-methylheptanoyloxy)phenyl]pyrimidine.

73. The compound of claim 9, which is (s)-2-(4-n-octyloxyphenyl)-5-(6'-methyloctyl)pyrimidine.

74. The compound of claim 10, which is (s)-2-(4-n-octylphenyl)-5-(6'-methyloctyloxy)pyrimidine.

75. The compound of claim 11, which is (s)-5-n-octyloxycarbonyl-2-[4-(6'-methyloctyloxy)phenyl]pyrimidine.

76. The compound of claim 12, which is (s)-5-(6'-methyloctyloxycarbonyl)-2-(4'-n-octyloxyphenyl)pyrimidine.

77. The compound of claim 13, which is (s)-2-(4-n-undecyloxyphenyl)-5-(2'methylbutyloxy)pyrimidine.

78. The compound of claim 14, which is (s)-2-(4-n-undecanoyloxyphenyl)-5-(2'-methylbutyloxy)pyrimidine.

* * * * *